(12) United States Patent
Robertson et al.

(10) Patent No.: US 9,107,689 B2
(45) Date of Patent: Aug. 18, 2015

(54) DUAL PURPOSE SURGICAL INSTRUMENT FOR CUTTING AND COAGULATING TISSUE

(71) Applicant: Ethicon Endo-Surgery, Inc., Cincinnati, OH (US)

(72) Inventors: Galen C. Robertson, Apex, NC (US); Richard W. Timm, Cincinnati, OH (US); Kevin L. Houser, Springboro, OH (US); Sean P. Conlon, Loveland, OH (US); Aron O. Zingman, Cambridge, MA (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 13/942,103

(22) Filed: Jul. 15, 2013

(65) Prior Publication Data

US 2013/0345733 A1 Dec. 26, 2013

Related U.S. Application Data

(62) Division of application No. 12/703,879, filed on Feb. 11, 2010, now Pat. No. 8,486,096.

(51) Int. Cl.
*A61B 17/32* (2006.01)
*A61B 17/3207* (2006.01)

(52) U.S. Cl.
CPC ..... *A61B 17/320068* (2013.01); *A61B 17/3207* (2013.01); *A61B 17/320783* (2013.01)

(58) Field of Classification Search
CPC .............. A61B 17/320068; A61B 17/320092; A61B 17/3207; A61B 17/320758; A61B 17/320783

USPC .............. 606/167, 169–171, 180, 37; 604/22; 600/562–568

See application file for complete search history.

(56) References Cited

U.S. PATENT DOCUMENTS

| | | | |
|---|---|---|---|
| 969,528 A | 9/1910 | Disbrow |
| 1,570,025 A | 1/1926 | Young |
| 2,704,333 A | 3/1955 | Calosi et al. |
| 2,736,960 A | 3/1956 | Armstrong |
| 2,849,788 A | 9/1958 | Creek |

(Continued)

FOREIGN PATENT DOCUMENTS

| | | |
|---|---|---|
| CN | 1634601 A | 7/2005 |
| CN | 1640365 A | 7/2005 |

(Continued)

OTHER PUBLICATIONS

International Search Report for PCT/US2011/024206, Apr. 27, 2011 included in PCT Publication No. WO 2011/100335 A1 (44 pages).

(Continued)

*Primary Examiner* — Ryan Severson

(57) ABSTRACT

In one general aspect, various embodiments are directed to an ultrasonic surgical instrument that has an ultrasonic blade that protrudes from an ultrasonic transducer assembly. In some embodiments, the ultrasonic blade coaxially extends through a rotatable tissue cutting blade that is rotatably supported by a housing that supports the ultrasonic transducer assembly. In other embodiments, the ultrasonic blade and the tissue cutting blade are both selectively rotatable relative to the housing. In yet other embodiments, the tissue cutting blade and the ultrasonic blade are supported relative to each other in separate sheaths attached to the housing.

19 Claims, 10 Drawing Sheets

(56) References Cited

U.S. PATENT DOCUMENTS

| | | | |
|---|---|---|---|
| RE25,033 E | 8/1961 | Balamuth et al. | |
| 3,015,961 A | 1/1962 | Roney | |
| 3,053,124 A | 9/1962 | Balamuth et al. | |
| 3,082,805 A * | 3/1963 | Royce | 241/260.1 |
| 3,513,848 A | 5/1970 | Winston et al. | |
| 3,526,219 A | 9/1970 | Balamuth | |
| 3,554,198 A | 1/1971 | Tatoian et al. | |
| 3,614,484 A | 10/1971 | Shoh | |
| 3,636,943 A | 1/1972 | Balamuth | |
| 3,702,948 A | 11/1972 | Balamuth | |
| 3,776,238 A * | 12/1973 | Peyman et al. | 606/171 |
| 3,805,787 A * | 4/1974 | Banko | 604/22 |
| 3,830,098 A | 8/1974 | Antonevich | |
| 3,854,737 A | 12/1974 | Gilliam, Sr. | |
| 3,862,630 A | 1/1975 | Balamuth | |
| 3,900,823 A | 8/1975 | Sokal et al. | |
| 3,918,442 A | 11/1975 | Nikolaev et al. | |
| 3,946,738 A | 3/1976 | Newton et al. | |
| 3,955,859 A | 5/1976 | Stella et al. | |
| 3,956,826 A | 5/1976 | Perdreaux, Jr. | |
| 4,074,719 A | 2/1978 | Semm | |
| 4,156,187 A | 5/1979 | Murry et al. | |
| 4,167,944 A * | 9/1979 | Banko | 606/107 |
| 4,188,927 A | 2/1980 | Harris | |
| 4,200,106 A * | 4/1980 | Douvas et al. | 606/168 |
| 4,203,444 A * | 5/1980 | Bonnell et al. | 604/22 |
| 4,306,570 A * | 12/1981 | Matthews | 600/567 |
| 4,445,063 A | 4/1984 | Smith | |
| 4,491,132 A | 1/1985 | Aikins | |
| 4,504,264 A | 3/1985 | Kelman | |
| 4,512,344 A * | 4/1985 | Barber | 606/79 |
| 4,574,615 A | 3/1986 | Bower et al. | |
| 4,617,927 A | 10/1986 | Manes | |
| 4,633,119 A | 12/1986 | Thompson | |
| 4,634,420 A | 1/1987 | Spinosa et al. | |
| 4,640,279 A | 2/1987 | Beard | |
| 4,646,738 A * | 3/1987 | Trott | 606/170 |
| 4,649,919 A * | 3/1987 | Thimsen et al. | 606/80 |
| 4,662,068 A | 5/1987 | Polonsky | |
| 4,674,502 A * | 6/1987 | Imonti | 606/177 |
| 4,708,127 A | 11/1987 | Abdelghani | |
| 4,712,722 A | 12/1987 | Hood et al. | |
| 4,819,635 A * | 4/1989 | Shapiro | 606/170 |
| 4,827,911 A | 5/1989 | Broadwin et al. | |
| 4,832,683 A | 5/1989 | Idemoto et al. | |
| 4,836,186 A | 6/1989 | Scholz | |
| 4,838,853 A | 6/1989 | Parisi | |
| 4,844,064 A * | 7/1989 | Thimsen et al. | 606/80 |
| 4,850,354 A * | 7/1989 | McGurk-Burleson et al. | 606/170 |
| 4,852,578 A | 8/1989 | Companion et al. | |
| 4,865,159 A | 9/1989 | Jamison | |
| 4,867,157 A * | 9/1989 | McGurk-Burleson et al. | 606/170 |
| 4,878,493 A | 11/1989 | Pasternak et al. | |
| 4,881,550 A * | 11/1989 | Kothe | 600/565 |
| 4,896,009 A | 1/1990 | Pawlowski | |
| 4,903,696 A | 2/1990 | Stasz et al. | |
| 4,915,643 A | 4/1990 | Samejima et al. | |
| 4,922,902 A | 5/1990 | Wuchinich et al. | |
| 4,965,532 A | 10/1990 | Sakurai | |
| 4,979,952 A | 12/1990 | Kubota et al. | |
| 4,981,756 A | 1/1991 | Rhandhawa | |
| 5,013,956 A | 5/1991 | Kurozumi et al. | |
| 5,015,227 A | 5/1991 | Broadwin et al. | |
| 5,026,387 A | 6/1991 | Thomas | |
| 5,042,707 A | 8/1991 | Taheri | |
| 5,084,052 A * | 1/1992 | Jacobs | 606/79 |
| 5,105,117 A | 4/1992 | Yamaguchi | |
| 5,109,819 A | 5/1992 | Custer et al. | |
| 5,112,300 A | 5/1992 | Ureche | |
| 5,123,903 A | 6/1992 | Quaid et al. | |
| 5,126,618 A | 6/1992 | Takahashi et al. | |
| D327,872 S | 7/1992 | McMills et al. | |
| 5,162,044 A | 11/1992 | Gahn et al. | |
| 5,163,537 A | 11/1992 | Radev | |
| 5,167,725 A | 12/1992 | Clark et al. | |
| 5,174,276 A | 12/1992 | Crockard | |
| D332,660 S | 1/1993 | Rawson et al. | |
| 5,176,677 A | 1/1993 | Wuchinich | |
| 5,176,695 A | 1/1993 | Dulebohn | |
| 5,184,605 A | 2/1993 | Grzeszykowski | |
| 5,188,102 A | 2/1993 | Idemoto et al. | |
| D334,173 S | 3/1993 | Liu et al. | |
| 5,209,719 A | 5/1993 | Baruch et al. | |
| 5,213,569 A | 5/1993 | Davis | |
| 5,214,339 A | 5/1993 | Naito | |
| 5,218,529 A | 6/1993 | Meyer et al. | |
| 5,221,282 A | 6/1993 | Wuchinich | |
| 5,226,909 A * | 7/1993 | Evans et al. | 606/159 |
| 5,226,910 A * | 7/1993 | Kajiyama et al. | 606/171 |
| 5,241,236 A | 8/1993 | Sasaki et al. | |
| 5,241,968 A | 9/1993 | Slater | |
| 5,242,460 A * | 9/1993 | Klein et al. | 606/159 |
| 5,254,129 A | 10/1993 | Alexander | |
| 5,257,988 A | 11/1993 | L'Esperance, Jr. | |
| 5,261,922 A | 11/1993 | Hood | |
| 5,263,957 A | 11/1993 | Davison | |
| 5,275,609 A * | 1/1994 | Pingleton et al. | 606/170 |
| 5,282,800 A | 2/1994 | Foshee et al. | |
| 5,282,817 A | 2/1994 | Hoogeboom et al. | |
| 5,285,795 A * | 2/1994 | Ryan et al. | 600/563 |
| 5,304,115 A | 4/1994 | Pflueger et al. | |
| D347,474 S | 5/1994 | Olson | |
| 5,312,023 A | 5/1994 | Green et al. | |
| 5,312,425 A * | 5/1994 | Evans et al. | 606/159 |
| 5,322,055 A | 6/1994 | Davison et al. | |
| 5,324,299 A | 6/1994 | Davison et al. | |
| 5,326,013 A | 7/1994 | Green et al. | |
| 5,326,342 A | 7/1994 | Pflueger et al. | |
| 5,344,420 A | 9/1994 | Hilal et al. | |
| 5,345,937 A | 9/1994 | Middleman et al. | |
| 5,346,502 A | 9/1994 | Estabrook et al. | |
| 5,353,474 A | 10/1994 | Good et al. | |
| 5,357,164 A | 10/1994 | Imabayashi et al. | |
| 5,357,423 A | 10/1994 | Weaver et al. | |
| 5,359,994 A | 11/1994 | Krauter et al. | |
| 5,366,466 A | 11/1994 | Christian et al. | |
| 5,371,429 A | 12/1994 | Manna | |
| D354,564 S | 1/1995 | Medema | |
| 5,381,067 A | 1/1995 | Greenstein et al. | |
| 5,387,215 A * | 2/1995 | Fisher | 606/79 |
| 5,403,312 A | 4/1995 | Yates et al. | |
| 5,403,334 A * | 4/1995 | Evans et al. | 606/159 |
| D358,887 S | 5/1995 | Feinberg | |
| 5,411,481 A | 5/1995 | Allen et al. | |
| 5,419,761 A | 5/1995 | Narayanan et al. | |
| 5,421,829 A | 6/1995 | Olichney et al. | |
| 5,423,844 A * | 6/1995 | Miller | 606/171 |
| 5,438,997 A | 8/1995 | Sieben et al. | |
| 5,445,639 A * | 8/1995 | Kuslich et al. | 606/80 |
| 5,449,370 A | 9/1995 | Vaitekunas | |
| 5,456,684 A | 10/1995 | Schmidt et al. | |
| 5,471,988 A | 12/1995 | Fujio et al. | |
| 5,478,003 A | 12/1995 | Green et al. | |
| 5,483,501 A | 1/1996 | Park et al. | |
| 5,486,162 A | 1/1996 | Brumbach | |
| 5,500,216 A | 3/1996 | Julian et al. | |
| 5,501,654 A | 3/1996 | Failla et al. | |
| 5,505,693 A | 4/1996 | Mackool | |
| 5,507,738 A | 4/1996 | Ciervo | |
| 5,527,331 A | 6/1996 | Kresch et al. | |
| 5,540,693 A * | 7/1996 | Fisher | 606/79 |
| 5,558,671 A | 9/1996 | Yates | |
| 5,562,609 A | 10/1996 | Brumbach | |
| 5,562,610 A | 10/1996 | Brumbach | |
| 5,573,424 A | 11/1996 | Poppe | |
| 5,577,654 A | 11/1996 | Bishop | |
| 5,591,187 A * | 1/1997 | Dekel | 606/180 |
| 5,601,601 A | 2/1997 | Tal et al. | |
| 5,603,773 A | 2/1997 | Campbell | |
| 5,607,436 A | 3/1997 | Pratt et al. | |
| 5,618,492 A | 4/1997 | Auten et al. | |
| 5,620,447 A * | 4/1997 | Smith et al. | 606/79 |

(56) References Cited

U.S. PATENT DOCUMENTS

| | | | |
|---|---|---|---|
| 5,626,595 A | 5/1997 | Sklar et al. | |
| 5,628,760 A | 5/1997 | Knoepfler | |
| 5,630,420 A | 5/1997 | Vaitekunas | |
| D381,077 S | 7/1997 | Hunt | |
| 5,651,780 A | 7/1997 | Jackson et al. | |
| 5,653,713 A | 8/1997 | Michelson | |
| 5,669,922 A | 9/1997 | Hood | |
| 5,674,235 A * | 10/1997 | Parisi | 606/169 |
| 5,678,568 A | 10/1997 | Uchikubo et al. | |
| 5,690,269 A | 11/1997 | Bolanos et al. | |
| 5,694,936 A | 12/1997 | Fujimoto et al. | |
| 5,711,472 A | 1/1998 | Bryan | |
| 5,713,896 A | 2/1998 | Nardella | |
| 5,730,752 A * | 3/1998 | Alden et al. | 606/180 |
| 5,733,074 A | 3/1998 | Stöck et al. | |
| 5,741,226 A | 4/1998 | Strukel et al. | |
| 5,766,164 A | 6/1998 | Mueller et al. | |
| 5,792,135 A | 8/1998 | Madhani et al. | |
| 5,792,138 A | 8/1998 | Shipp | |
| 5,792,165 A | 8/1998 | Klieman et al. | |
| 5,808,396 A | 9/1998 | Boukhny | |
| 5,810,859 A | 9/1998 | DiMatteo et al. | |
| 5,817,084 A | 10/1998 | Jensen | |
| 5,817,119 A | 10/1998 | Klieman et al. | |
| 5,827,323 A | 10/1998 | Klieman et al. | |
| 5,828,160 A | 10/1998 | Sugishita | |
| 5,833,696 A | 11/1998 | Whitfield et al. | |
| 5,836,897 A | 11/1998 | Sakurai et al. | |
| 5,836,957 A * | 11/1998 | Schulz et al. | 606/159 |
| 5,843,109 A | 12/1998 | Mehta et al. | |
| 5,851,212 A * | 12/1998 | Zirps et al. | 606/167 |
| 5,873,873 A | 2/1999 | Smith et al. | |
| 5,873,882 A * | 2/1999 | Straub et al. | 606/159 |
| 5,878,193 A | 3/1999 | Wang et al. | |
| 5,879,364 A | 3/1999 | Bromfield et al. | |
| 5,883,615 A | 3/1999 | Fago et al. | |
| 5,893,835 A | 4/1999 | Witt et al. | |
| 5,897,523 A | 4/1999 | Wright et al. | |
| 5,897,569 A | 4/1999 | Kellogg et al. | |
| 5,904,681 A * | 5/1999 | West, Jr. | 606/41 |
| 5,906,627 A * | 5/1999 | Spaulding | 606/159 |
| 5,906,628 A * | 5/1999 | Miyawaki et al. | 606/169 |
| 5,911,699 A | 6/1999 | Anis et al. | |
| 5,916,229 A * | 6/1999 | Evans | 606/171 |
| 5,935,143 A | 8/1999 | Hood | |
| 5,935,144 A | 8/1999 | Estabrook | |
| 5,938,633 A | 8/1999 | Beaupre | |
| 5,944,718 A | 8/1999 | Austin et al. | |
| 5,944,737 A | 8/1999 | Tsonton et al. | |
| 5,947,984 A | 9/1999 | Whipple | |
| 5,954,736 A | 9/1999 | Bishop et al. | |
| 5,954,746 A | 9/1999 | Holthaus et al. | |
| 5,957,882 A | 9/1999 | Nita et al. | |
| 5,957,943 A | 9/1999 | Vaitekunas | |
| 5,968,007 A | 10/1999 | Simon et al. | |
| 5,968,060 A | 10/1999 | Kellogg | |
| 5,974,342 A | 10/1999 | Petrofsky | |
| D416,089 S | 11/1999 | Barton et al. | |
| 5,980,510 A | 11/1999 | Tsonton et al. | |
| 5,980,546 A * | 11/1999 | Hood | 606/171 |
| 5,989,274 A | 11/1999 | Davison et al. | |
| 5,989,275 A | 11/1999 | Estabrook et al. | |
| 5,993,972 A | 11/1999 | Reich et al. | |
| 6,024,741 A | 2/2000 | Williamson, IV et al. | |
| 6,024,750 A | 2/2000 | Mastri et al. | |
| 6,027,515 A | 2/2000 | Cimino | |
| 6,033,375 A | 3/2000 | Brumbach | |
| 6,033,399 A | 3/2000 | Gines | |
| 6,036,667 A | 3/2000 | Manna et al. | |
| 6,036,707 A * | 3/2000 | Spaulding | 606/159 |
| 6,048,224 A | 4/2000 | Kay | |
| 6,050,943 A | 4/2000 | Slayton et al. | |
| 6,051,010 A | 4/2000 | DiMatteo et al. | |
| 6,056,735 A | 5/2000 | Okada et al. | |
| 6,063,098 A | 5/2000 | Houser et al. | |
| 6,066,132 A | 5/2000 | Chen et al. | |
| 6,066,151 A | 5/2000 | Miyawaki et al. | |
| 6,068,627 A | 5/2000 | Orszulak et al. | |
| 6,068,647 A | 5/2000 | Witt et al. | |
| 6,077,285 A | 6/2000 | Boukhny | |
| 6,083,191 A | 7/2000 | Rose | |
| 6,086,584 A | 7/2000 | Miller | |
| 6,090,120 A | 7/2000 | Wright et al. | |
| 6,099,542 A * | 8/2000 | Cohn et al. | 606/167 |
| 6,109,500 A | 8/2000 | Alli et al. | |
| 6,110,127 A | 8/2000 | Suzuki | |
| 6,113,594 A | 9/2000 | Savage | |
| 6,117,152 A | 9/2000 | Huitema | |
| 6,126,629 A | 10/2000 | Perkins | |
| 6,129,735 A | 10/2000 | Okada et al. | |
| 6,132,368 A | 10/2000 | Cooper | |
| 6,132,448 A | 10/2000 | Perez et al. | |
| 6,139,320 A | 10/2000 | Hahn | |
| 6,139,561 A | 10/2000 | Shibata et al. | |
| 6,142,615 A | 11/2000 | Qiu et al. | |
| 6,142,994 A | 11/2000 | Swanson et al. | |
| 6,147,560 A | 11/2000 | Erhage et al. | |
| 6,152,902 A | 11/2000 | Christian et al. | |
| 6,159,160 A | 12/2000 | Hsei et al. | |
| 6,159,175 A | 12/2000 | Strukel et al. | |
| 6,165,150 A | 12/2000 | Banko | |
| 6,174,310 B1 | 1/2001 | Kirwan, Jr. | |
| 6,179,853 B1 * | 1/2001 | Sachse et al. | 606/171 |
| 6,204,592 B1 | 3/2001 | Hur | |
| 6,205,855 B1 | 3/2001 | Pfeiffer | |
| 6,206,844 B1 | 3/2001 | Reichel et al. | |
| 6,210,403 B1 | 4/2001 | Klicek | |
| 6,214,023 B1 | 4/2001 | Whipple et al. | |
| 6,231,565 B1 | 5/2001 | Tovey et al. | |
| 6,233,476 B1 | 5/2001 | Strommer et al. | |
| 6,238,366 B1 | 5/2001 | Savage et al. | |
| 6,245,065 B1 | 6/2001 | Panescu et al. | |
| 6,252,110 B1 | 6/2001 | Uemura et al. | |
| D444,365 S | 7/2001 | Bass et al. | |
| D445,092 S | 7/2001 | Lee | |
| D445,764 S | 7/2001 | Lee | |
| 6,254,623 B1 | 7/2001 | Haibel, Jr. et al. | |
| 6,258,034 B1 | 7/2001 | Hanafy | |
| 6,267,761 B1 | 7/2001 | Ryan | |
| 6,270,831 B2 | 8/2001 | Kumar et al. | |
| 6,273,852 B1 | 8/2001 | Lehe et al. | |
| 6,274,963 B1 | 8/2001 | Estabrook et al. | |
| 6,277,115 B1 | 8/2001 | Saadat | |
| 6,278,218 B1 | 8/2001 | Madan et al. | |
| 6,283,981 B1 | 9/2001 | Beaupre | |
| 6,319,221 B1 | 11/2001 | Savage et al. | |
| 6,325,795 B1 | 12/2001 | Lindemann et al. | |
| 6,325,799 B1 | 12/2001 | Goble | |
| 6,325,811 B1 | 12/2001 | Messerly | |
| 6,328,751 B1 | 12/2001 | Beaupre | |
| 6,338,657 B1 | 1/2002 | Harper et al. | |
| 6,340,352 B1 | 1/2002 | Okada et al. | |
| 6,352,532 B1 | 3/2002 | Kramer et al. | |
| 6,364,888 B1 | 4/2002 | Niemeyer et al. | |
| 6,379,320 B1 | 4/2002 | Lafon et al. | |
| D457,958 S | 5/2002 | Dycus et al. | |
| 6,383,194 B1 | 5/2002 | Pothula | |
| 6,387,109 B1 | 5/2002 | Davison et al. | |
| 6,388,657 B1 | 5/2002 | Natoli | |
| 6,391,042 B1 | 5/2002 | Cimino | |
| 6,402,743 B1 | 6/2002 | Orszulak et al. | |
| 6,402,748 B1 | 6/2002 | Schoenman et al. | |
| 6,405,733 B1 | 6/2002 | Fogarty et al. | |
| 6,416,486 B1 | 7/2002 | Wampler | |
| 6,423,073 B2 | 7/2002 | Bowman | |
| 6,423,082 B1 | 7/2002 | Houser et al. | |
| 6,428,539 B1 * | 8/2002 | Baxter et al. | 606/49 |
| 6,432,118 B1 * | 8/2002 | Messerly | 606/169 |
| 6,436,114 B1 | 8/2002 | Novak et al. | |
| 6,436,115 B1 | 8/2002 | Beaupre | |
| 6,440,062 B1 | 8/2002 | Ouchi | |
| 6,443,969 B1 | 9/2002 | Novak et al. | |
| 6,454,781 B1 | 9/2002 | Witt et al. | |
| 6,454,782 B1 | 9/2002 | Schwemberger | |

(56) References Cited

U.S. PATENT DOCUMENTS

| | | | |
|---|---|---|---|
| 6,458,142 | B1 | 10/2002 | Faller et al. |
| 6,480,796 | B2 | 11/2002 | Wiener |
| 6,485,490 | B2 | 11/2002 | Wampler et al. |
| 6,491,708 | B2 | 12/2002 | Madan et al. |
| 6,497,715 | B2 | 12/2002 | Satou |
| 6,500,176 | B1 | 12/2002 | Truckai et al. |
| 6,500,188 | B2 | 12/2002 | Harper et al. |
| 6,500,312 | B2 | 12/2002 | Wedekamp |
| 6,506,208 | B2 | 1/2003 | Hunt et al. |
| 6,511,493 | B1 * | 1/2003 | Moutafis et al. ............ 606/167 |
| 6,514,267 | B2 | 2/2003 | Jewett |
| 6,524,251 | B2 | 2/2003 | Rabiner et al. |
| 6,524,316 | B1 | 2/2003 | Nicholson et al. |
| 6,527,736 | B1 * | 3/2003 | Attinger et al. ............... 604/43 |
| 6,533,784 | B2 | 3/2003 | Truckai et al. |
| 6,537,291 | B2 | 3/2003 | Friedman et al. |
| 6,543,452 | B1 | 4/2003 | Lavigne |
| 6,543,456 | B1 | 4/2003 | Freeman |
| 6,544,260 | B1 | 4/2003 | Markel et al. |
| 6,558,376 | B2 | 5/2003 | Bishop |
| 6,561,983 | B2 | 5/2003 | Cronin et al. |
| 6,572,563 | B2 * | 6/2003 | Ouchi ............................ 600/564 |
| 6,572,632 | B2 | 6/2003 | Zisterer et al. |
| 6,575,969 | B1 | 6/2003 | Rittman, III et al. |
| 6,582,451 | B1 | 6/2003 | Marucci et al. |
| D477,408 | S | 7/2003 | Bromley |
| 6,589,200 | B1 | 7/2003 | Schwemberger et al. |
| 6,589,239 | B2 | 7/2003 | Khandkar et al. |
| 6,610,059 | B1 | 8/2003 | West, Jr. |
| 6,616,450 | B2 | 9/2003 | Mossle et al. |
| 6,619,529 | B2 | 9/2003 | Green et al. |
| 6,623,500 | B1 | 9/2003 | Cook et al. |
| 6,623,501 | B2 | 9/2003 | Heller et al. |
| 6,626,926 | B2 | 9/2003 | Friedman et al. |
| 6,633,234 | B2 | 10/2003 | Wiener et al. |
| 6,644,532 | B2 | 11/2003 | Green et al. |
| 6,656,132 | B1 * | 12/2003 | Ouchi ............................ 600/564 |
| 6,656,177 | B2 | 12/2003 | Truckai et al. |
| 6,662,127 | B2 | 12/2003 | Wiener et al. |
| 6,663,941 | B2 | 12/2003 | Brown et al. |
| 6,666,860 | B1 | 12/2003 | Takahashi |
| 6,666,875 | B1 | 12/2003 | Sakurai et al. |
| 6,669,690 | B1 | 12/2003 | Okada et al. |
| 6,676,660 | B2 | 1/2004 | Wampler et al. |
| 6,678,621 | B2 | 1/2004 | Wiener et al. |
| 6,679,875 | B2 | 1/2004 | Honda et al. |
| 6,679,899 | B2 | 1/2004 | Wiener et al. |
| 6,682,544 | B2 | 1/2004 | Mastri et al. |
| 6,685,701 | B2 | 2/2004 | Orszulak et al. |
| 6,685,703 | B2 | 2/2004 | Pearson et al. |
| 6,689,146 | B1 | 2/2004 | Himes |
| 6,716,215 | B1 | 4/2004 | David et al. |
| D490,059 | S | 5/2004 | Conway et al. |
| 6,731,047 | B2 | 5/2004 | Kauf et al. |
| 6,733,506 | B1 | 5/2004 | McDevitt et al. |
| D491,666 | S | 6/2004 | Kimmell et al. |
| 6,743,245 | B2 * | 6/2004 | Lobdell ......................... 606/171 |
| 6,746,284 | B1 | 6/2004 | Spink, Jr. |
| 6,752,815 | B2 | 6/2004 | Beaupre |
| 6,755,825 | B2 | 6/2004 | Shoenman et al. |
| 6,761,698 | B2 | 7/2004 | Shibata et al. |
| 6,762,535 | B2 | 7/2004 | Take et al. |
| 6,770,072 | B1 | 8/2004 | Truckai et al. |
| 6,773,409 | B2 | 8/2004 | Truckai et al. |
| 6,773,443 | B2 * | 8/2004 | Truwit et al. ................ 606/169 |
| 6,773,444 | B2 | 8/2004 | Messerly |
| 6,778,023 | B2 | 8/2004 | Christensen |
| 6,783,524 | B2 | 8/2004 | Anderson et al. |
| 6,786,382 | B1 | 9/2004 | Hoffman |
| 6,786,383 | B2 | 9/2004 | Stegelmann |
| 6,790,173 | B2 | 9/2004 | Saadat et al. |
| 6,790,216 | B1 | 9/2004 | Ishikawa |
| D496,997 | S | 10/2004 | Dycus et al. |
| 6,802,843 | B2 | 10/2004 | Truckai et al. |
| 6,809,508 | B2 | 10/2004 | Donofrio |
| 6,827,712 | B2 | 12/2004 | Tovey et al. |
| 6,828,712 | B2 | 12/2004 | Battaglin et al. |
| 6,835,082 | B2 | 12/2004 | Gonnering |
| 6,849,073 | B2 | 2/2005 | Hoey et al. |
| 6,869,439 | B2 | 3/2005 | White et al. |
| 6,875,220 | B2 | 4/2005 | Du et al. |
| 6,877,647 | B2 | 4/2005 | Green et al. |
| 6,882,439 | B2 | 4/2005 | Ishijima |
| 6,887,209 | B2 * | 5/2005 | Kadziauskas et al. ........ 600/565 |
| 6,899,685 | B2 * | 5/2005 | Kermode et al. ............. 600/564 |
| 6,905,497 | B2 | 6/2005 | Truckai et al. |
| 6,908,472 | B2 | 6/2005 | Wiener et al. |
| 6,913,579 | B2 | 7/2005 | Truckai et al. |
| 6,923,804 | B2 | 8/2005 | Eggers et al. |
| 6,926,716 | B2 | 8/2005 | Baker et al. |
| 6,929,632 | B2 | 8/2005 | Nita et al. |
| 6,929,644 | B2 | 8/2005 | Truckai et al. |
| 6,933,656 | B2 | 8/2005 | Matsushita et al. |
| D509,589 | S | 9/2005 | Wells |
| 6,942,677 | B2 | 9/2005 | Nita et al. |
| 6,945,981 | B2 | 9/2005 | Donofrio et al. |
| 6,946,779 | B2 | 9/2005 | Birgel |
| D511,145 | S | 11/2005 | Donofrio et al. |
| 6,974,450 | B2 | 12/2005 | Weber et al. |
| 6,976,844 | B2 | 12/2005 | Hickok et al. |
| 6,976,969 | B2 | 12/2005 | Messerly |
| 6,977,495 | B2 | 12/2005 | Donofrio |
| 6,979,332 | B2 * | 12/2005 | Adams ............................ 606/45 |
| 6,984,220 | B2 | 1/2006 | Wuchinich |
| 6,994,708 | B2 | 2/2006 | Manzo |
| 7,001,335 | B2 | 2/2006 | Adachi et al. |
| 7,011,657 | B2 | 3/2006 | Truckai et al. |
| 7,014,638 | B2 | 3/2006 | Michelson |
| 7,041,083 | B2 | 5/2006 | Chu et al. |
| 7,041,088 | B2 | 5/2006 | Nawrocki et al. |
| 7,041,102 | B2 | 5/2006 | Truckai et al. |
| 7,044,949 | B2 | 5/2006 | Orszulak et al. |
| 7,066,893 | B2 * | 6/2006 | Hibner et al. .................. 600/566 |
| 7,070,597 | B2 | 7/2006 | Truckai et al. |
| 7,074,219 | B2 | 7/2006 | Levine et al. |
| 7,077,039 | B2 | 7/2006 | Gass et al. |
| 7,077,853 | B2 | 7/2006 | Kramer et al. |
| 7,083,619 | B2 | 8/2006 | Truckai et al. |
| 7,087,054 | B2 | 8/2006 | Truckai et al. |
| 7,090,672 | B2 | 8/2006 | Underwood et al. |
| 7,101,371 | B2 | 9/2006 | Dycus et al. |
| 7,101,378 | B2 * | 9/2006 | Salameh et al. .............. 606/113 |
| 7,104,834 | B2 | 9/2006 | Robinson et al. |
| 7,108,695 | B2 | 9/2006 | Witt et al. |
| 7,111,769 | B2 | 9/2006 | Wales et al. |
| 7,112,201 | B2 | 9/2006 | Truckai et al. |
| D531,311 | S | 10/2006 | Guerra et al. |
| 7,117,034 | B2 | 10/2006 | Kronberg |
| 7,118,564 | B2 | 10/2006 | Ritchie et al. |
| 7,124,932 | B2 | 10/2006 | Isaacson et al. |
| 7,125,409 | B2 | 10/2006 | Truckai et al. |
| 7,131,860 | B2 | 11/2006 | Sartor et al. |
| 7,135,018 | B2 | 11/2006 | Ryan et al. |
| 7,135,030 | B2 | 11/2006 | Schwemberger et al. |
| 7,144,403 | B2 | 12/2006 | Booth |
| 7,153,315 | B2 | 12/2006 | Miller |
| D536,093 | S | 1/2007 | Nakajima et al. |
| 7,156,189 | B1 | 1/2007 | Bar-Cohen et al. |
| 7,156,853 | B2 | 1/2007 | Muratsu |
| 7,157,058 | B2 | 1/2007 | Marhasin et al. |
| 7,159,750 | B2 | 1/2007 | Racenet et al. |
| 7,160,299 | B2 | 1/2007 | Baily |
| 7,163,548 | B2 | 1/2007 | Stulen et al. |
| 7,169,144 | B2 | 1/2007 | Hoey et al. |
| 7,169,146 | B2 | 1/2007 | Truckai et al. |
| 7,179,271 | B2 | 2/2007 | Friedman et al. |
| 7,186,253 | B2 | 3/2007 | Truckai et al. |
| 7,189,233 | B2 | 3/2007 | Truckai et al. |
| D541,418 | S | 4/2007 | Schechter et al. |
| 7,204,820 | B2 | 4/2007 | Akahoshi |
| 7,211,079 | B2 | 5/2007 | Treat |
| 7,217,269 | B2 | 5/2007 | El-Galley et al. |
| 7,220,951 | B2 | 5/2007 | Truckai et al. |
| 7,223,229 | B2 | 5/2007 | Inman et al. |

(56) References Cited

U.S. PATENT DOCUMENTS

| | | |
|---|---|---|
| 7,229,455 B2 | 6/2007 | Sakurai et al. |
| 7,235,071 B2 | 6/2007 | Gonnering |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,331,410 B2 | 2/2008 | Yong et al. |
| 7,353,068 B2 | 4/2008 | Tanaka et al. |
| 7,354,440 B2 | 4/2008 | Truckal et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2* | 1/2009 | Weikel et al. .......... 600/567 |
| 7,488,285 B2 | 2/2009 | Honda et al. |
| 7,494,468 B2 | 2/2009 | Rabiner et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,544,200 B2 | 6/2009 | Houser |
| 7,549,564 B2 | 6/2009 | Boudreaux |
| 7,559,450 B2 | 7/2009 | Wales et al. |
| 7,567,012 B2 | 7/2009 | Namikawa |
| 7,578,820 B2 | 8/2009 | Moore et al. |
| 7,588,176 B2 | 9/2009 | Timm et al. |
| 7,621,930 B2 | 11/2009 | Houser |
| 7,641,653 B2 | 1/2010 | Dalla Betta et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2* | 3/2010 | Albrecht et al. .......... 606/45 |
| 7,674,263 B2* | 3/2010 | Ryan .......... 606/50 |
| 7,678,069 B1 | 3/2010 | Baker et al. |
| 7,686,770 B2* | 3/2010 | Cohen .......... 600/568 |
| 7,686,826 B2 | 3/2010 | Lee et al. |
| 7,691,098 B2 | 4/2010 | Wallace et al. |
| 7,713,202 B2 | 5/2010 | Boukhny et al. |
| 7,714,481 B2 | 5/2010 | Sakai |
| D618,797 S | 6/2010 | Price et al. |
| 7,726,537 B2 | 6/2010 | Olson et al. |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,798,386 B2 | 9/2010 | Schall et al. |
| 7,803,152 B2 | 9/2010 | Honda et al. |
| 7,806,891 B2 | 10/2010 | Nowlin et al. |
| 7,810,693 B2 | 10/2010 | Broehl et al. |
| D627,066 S | 11/2010 | Romero |
| 7,824,401 B2 | 11/2010 | Manzo et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,892,606 B2 | 2/2011 | Thies et al. |
| 7,901,423 B2 | 3/2011 | Stulen et al. |
| 7,905,881 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,976,544 B2 | 7/2011 | McClurken et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,075,558 B2 | 12/2011 | Truckai et al. |
| 8,089,197 B2 | 1/2012 | Rinner et al. |
| 8,097,012 B2* | 1/2012 | Kagarise .......... 606/170 |
| 8,142,461 B2 | 3/2012 | Houser et al. |
| 8,152,825 B2 | 4/2012 | Madan et al. |
| 8,157,145 B2 | 4/2012 | Shelton, IV et al. |
| 8,162,966 B2 | 4/2012 | Connor et al. |
| 8,177,800 B2 | 5/2012 | Spitz et al. |
| 8,182,502 B2 | 5/2012 | Stulen et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,502 B2 | 6/2012 | Smith et al. |
| 8,226,675 B2 | 7/2012 | Houser et al. |
| 8,236,019 B2 | 8/2012 | Houser |
| 8,236,020 B2 | 8/2012 | Smith et al. |
| 8,246,575 B2 | 8/2012 | Viola |
| 8,252,012 B2 | 8/2012 | Stulen |
| 8,253,303 B2 | 8/2012 | Giordano et al. |
| 8,257,377 B2 | 9/2012 | Wiener et al. |
| D669,992 S | 10/2012 | Schafer et al. |
| D669,993 S | 10/2012 | Merchant et al. |
| 8,287,485 B2 | 10/2012 | Kimura et al. |
| 8,287,532 B2 | 10/2012 | Carroll et al. |
| 8,303,576 B2 | 11/2012 | Brock |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,372,101 B2 | 2/2013 | Smith et al. |
| 8,372,102 B2 | 2/2013 | Stulen et al. |
| 8,374,670 B2 | 2/2013 | Selkee |

(56) References Cited

U.S. PATENT DOCUMENTS

| | | |
|---|---|---|
| 8,377,059 B2 | 2/2013 | Deville et al. |
| 8,377,085 B2 | 2/2013 | Smith et al. |
| 8,382,782 B2 | 2/2013 | Robertson et al. |
| 8,418,349 B2 | 4/2013 | Smith et al. |
| 8,419,759 B2 | 4/2013 | Dietz |
| 8,430,898 B2 | 4/2013 | Wiener et al. |
| 8,439,912 B2 | 5/2013 | Cunningham et al. |
| 8,439,939 B2 | 5/2013 | Deville et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,485,413 B2 | 7/2013 | Scheib et al. |
| 8,486,096 B2 | 7/2013 | Robertson et al. |
| D687,549 S | 8/2013 | Johnson et al. |
| 8,512,365 B2 | 8/2013 | Wiener et al. |
| 8,523,889 B2 | 9/2013 | Stulen et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,536 B2 | 11/2013 | Robertson |
| D695,407 S | 12/2013 | Price et al. |
| D696,631 S | 12/2013 | Price et al. |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,663,220 B2 | 3/2014 | Wiener et al. |
| 2001/0005778 A1* | 6/2001 | Ouchi ............................ 600/564 |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0027325 A1* | 10/2001 | Beaupre ......................... 606/169 |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1* | 3/2002 | Bonutti ......................... 606/170 |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0077642 A1* | 6/2002 | Patel et al. ..................... 606/167 |
| 2002/0077648 A1* | 6/2002 | Lee et al. ...................... 606/170 |
| 2002/0099399 A1* | 7/2002 | Lee et al. ...................... 606/167 |
| 2002/0143269 A1* | 10/2002 | Neuenfeldt ................... 600/564 |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0040763 A1* | 2/2003 | Moutafis et al. .............. 606/167 |
| 2003/0050572 A1* | 3/2003 | Brautigam et al. ........... 600/565 |
| 2003/0055443 A1 | 3/2003 | Spotnitz |
| 2003/0114851 A1 | 6/2003 | Truckai et al. |
| 2003/0204199 A1 | 10/2003 | Novak et al. |
| 2003/0212332 A1 | 11/2003 | Fenton et al. |
| 2003/0212422 A1* | 11/2003 | Fenton et al. ................. 606/169 |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0059363 A1* | 3/2004 | Alvarez et al. ................ 606/170 |
| 2004/0064151 A1 | 4/2004 | Mollenauer |
| 2004/0092921 A1 | 5/2004 | Kadziauskas et al. |
| 2004/0092992 A1* | 5/2004 | Adams et al. ................. 606/180 |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0102772 A1* | 5/2004 | Baxter et al. .................. 606/45 |
| 2004/0167428 A1* | 8/2004 | Quick et al. .................. 600/564 |
| 2004/0167508 A1 | 8/2004 | Wham et al. |
| 2004/0176686 A1 | 9/2004 | Hare et al. |
| 2004/0176789 A1* | 9/2004 | Lee et al. ...................... 606/170 |
| 2004/0181251 A1* | 9/2004 | Hacker et al. ................. 606/170 |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2004/0260323 A1* | 12/2004 | Truwit et al. ................. 606/170 |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1* | 8/2005 | Lee et al. ...................... 600/564 |
| 2005/0188743 A1 | 9/2005 | Land |
| 2005/0192610 A1 | 9/2005 | Houser et al. |
| 2005/0209620 A1 | 9/2005 | Du et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074342 A1* | 4/2006 | Hibner ........................... 600/566 |
| 2006/0074442 A1 | 4/2006 | Noriega et al. |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0200123 A1* | 9/2006 | Ryan ............................. 606/48 |
| 2006/0206115 A1* | 9/2006 | Schomer et al. ............. 606/79 |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2006/0264809 A1 | 11/2006 | Hansmann et al. |
| 2006/0264927 A1* | 11/2006 | Ryan ............................. 606/45 |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106176 A1* | 5/2007 | Mark et al. .................... 600/566 |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0156064 A1* | 7/2007 | Ritchart et al. ............... 600/564 |
| 2007/0162050 A1 | 7/2007 | Sartor |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0051812 A1 | 2/2008 | Schmitz et al. |

(56) References Cited

U.S. PATENT DOCUMENTS

| | | |
|---|---|---|
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0125768 A1 | 5/2008 | Tahara et al. |
| 2008/0140158 A1 | 6/2008 | Hamel et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0234710 A1 | 9/2008 | Neurohr et al. |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281322 A1 | 11/2008 | Sherman et al. |
| 2008/0287948 A1 | 11/2008 | Newton et al. |
| 2009/0030437 A1 | 1/2009 | Houser et al. |
| 2009/0030439 A1 | 1/2009 | Stulen |
| 2009/0036914 A1 | 2/2009 | Houser |
| 2009/0048537 A1* | 2/2009 | Lydon et al. ............. 600/585 |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0112229 A1 | 4/2009 | Omori et al. |
| 2009/0118802 A1 | 5/2009 | Mioduski et al. |
| 2009/0125036 A1* | 5/2009 | Bleich ..................... 606/110 |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0149801 A1 | 6/2009 | Crandall et al. |
| 2009/0207923 A1 | 8/2009 | Dress |
| 2009/0234378 A1* | 9/2009 | Escudero et al. ............. 606/180 |
| 2009/0254077 A1 | 10/2009 | Craig |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318944 A1* | 12/2009 | Kimura et al. .............. 606/169 |
| 2009/0318945 A1* | 12/2009 | Yoshimine et al. .......... 606/169 |
| 2009/0327715 A1 | 12/2009 | Smith et al. |
| 2010/0004508 A1 | 1/2010 | Naito et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0268211 A1 | 10/2010 | Manwaring et al. |
| 2010/0274160 A1 | 10/2010 | Yachi et al. |
| 2010/0280407 A1* | 11/2010 | Polster ..................... 600/566 |
| 2010/0298743 A1 | 11/2010 | Nield et al. |
| 2010/0298851 A1 | 11/2010 | Nield |
| 2011/0004233 A1 | 1/2011 | Muir et al. |
| 2011/0009850 A1 | 1/2011 | Main et al. |
| 2011/0015627 A1 | 1/2011 | DiNardo et al. |
| 2011/0077648 A1 | 3/2011 | Lee et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0144806 A1 | 6/2011 | Sandhu et al. |
| 2011/0196398 A1 | 8/2011 | Robertson et al. |
| 2011/0196399 A1 | 8/2011 | Robertson et al. |
| 2011/0196404 A1 | 8/2011 | Dietz et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1* | 11/2011 | Gunday et al. ............. 600/565 |
| 2011/0290853 A1 | 12/2011 | Shelton, IV et al. |
| 2011/0290856 A1 | 12/2011 | Shelton, IV et al. |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0083783 A1 | 4/2012 | Davison et al. |
| 2012/0083784 A1 | 4/2012 | Davison et al. |
| 2012/0116379 A1 | 5/2012 | Yates et al. |
| 2012/0116395 A1 | 5/2012 | Madan et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0245582 A1 | 9/2012 | Kimball et al. |
| 2012/0259353 A1 | 10/2012 | Houser et al. |
| 2012/0265196 A1 | 10/2012 | Turner et al. |
| 2012/0269676 A1 | 10/2012 | Houser et al. |
| 2012/0310262 A1 | 12/2012 | Messerly et al. |
| 2012/0310264 A1 | 12/2012 | Messerly et al. |
| 2012/0323265 A1 | 12/2012 | Stulen |
| 2012/0330307 A1 | 12/2012 | Ladtkow et al. |
| 2013/0012957 A1 | 1/2013 | Shelton, IV et al. |
| 2013/0012970 A1 | 1/2013 | Houser |
| 2013/0030433 A1 | 1/2013 | Heard |
| 2013/0035680 A1 | 2/2013 | Ben-Haim et al. |
| 2013/0035706 A1 | 2/2013 | Giordano et al. |
| 2013/0035707 A1 | 2/2013 | Giordano et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |

(56) References Cited

U.S. PATENT DOCUMENTS

| | | |
|---|---|---|
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0178882 A1 | 7/2013 | Voegele et al. |
| 2013/0211397 A1 | 8/2013 | Parihar et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0245659 A1 | 9/2013 | Robertson et al. |
| 2013/0267975 A1 | 10/2013 | Timm et al. |
| 2013/0274732 A1 | 10/2013 | Wiener et al. |
| 2013/0274734 A1 | 10/2013 | Maass et al. |
| 2013/0282003 A1 | 10/2013 | Messerly et al. |
| 2013/0282039 A1 | 10/2013 | Wiener et al. |
| 2013/0285758 A1 | 10/2013 | Aldridge et al. |
| 2013/0289591 A1 | 10/2013 | Boudreaux et al. |
| 2013/0296908 A1 | 11/2013 | Schulte et al. |
| 2013/0345689 A1 | 12/2013 | Ruddenklau et al. |
| 2014/0005640 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005667 A1 | 1/2014 | Stulen et al. |
| 2014/0005668 A1 | 1/2014 | Rhee et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005682 A1 | 1/2014 | Worrell et al. |
| 2014/0005701 A1 | 1/2014 | Olson et al. |
| 2014/0005702 A1 | 1/2014 | Timm et al, |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0066962 A1 | 3/2014 | Robertson et al. |

FOREIGN PATENT DOCUMENTS

| | | | |
|---|---|---|---|
| CN | 1694649 A | 11/2005 | |
| CN | 1922563 A | 2/2007 | |
| CN | 1951333 A | 4/2007 | |
| CN | 101040799 A | 9/2007 | |
| DE | 9210327 U1 | 11/1992 | |
| DE | 19608716 C1 | 4/1997 | |
| DE | 20021619 U1 | 3/2001 | |
| DE | 10042606 A1 | 8/2001 | |
| EP | 0171967 A2 | 2/1986 | |
| EP | 1839599 A1 | 10/1987 | |
| EP | 0443256 A1 | 8/1991 | |
| EP | 0456470 A1 | 11/1991 | |
| EP | 0482195 B1 | 1/1996 | |
| EP | 0695535 A1 | 2/1996 | |
| EP | 0741996 A2 | 11/1996 | |
| EP | 0612570 B1 | 6/1997 | |
| EP | 1108394 A2 | 6/2001 | |
| EP | 0908148 B1 | 1/2002 | |
| EP | 0908155 B1 | 6/2003 | |
| EP | 1199044 B1 | 12/2005 | |
| EP | 1199043 B1 | 3/2006 | |
| EP | 1433425 B1 | 6/2006 | |
| EP | 1704824 A1 | 9/2006 | |
| EP | 1815950 A1 | 8/2007 | |
| EP | 1844720 A1 | 10/2007 | |
| EP | 1862133 A1 | 12/2007 | |
| EP | 1199045 B1 | 6/2008 | |
| EP | 1972264 A1 | 9/2008 | |
| EP | 1974771 A1 | 10/2008 | |
| EP | 1435852 B1 | 12/2008 | |
| EP | 1498082 B1 | 12/2008 | |
| EP | 2014218 A2 | 1/2009 | |
| EP | 2042112 A2 | 4/2009 | |
| EP | 1832259 B1 | 6/2009 | |
| EP | 2074959 A1 | 7/2009 | |
| EP | 1214913 B1 | 7/2010 | |
| EP | 2298154 A2 | 3/2011 | |
| EP | 1510178 B1 | 6/2011 | |
| EP | 2335630 A1 | 6/2011 | |
| EP | 2361562 A1 | 8/2011 | |
| EP | 2365608 A2 | 9/2011 | |
| EP | 2316359 B1 | 3/2013 | |
| GB | 2032221 A | 4/1980 | |
| GB | 2379878 B | 11/2004 | |
| GB | 2447767 B | 8/2011 | |
| JP | 62-221343 A | 9/1987 | |
| JP | 62-292153 A | 12/1987 | |
| JP | 63-109386 A | 5/1988 | |
| JP | 63-315049 A | 12/1988 | |
| JP | 02-71510 U | 5/1990 | |
| JP | 2-286149 A | 11/1990 | |
| JP | H 02-292193 A | 12/1990 | |
| JP | 04-25707 U | 2/1992 | |
| JP | 4-30508 U | 3/1992 | |
| JP | 05-095955 A | 4/1993 | |
| JP | H 06-070938 A | 3/1994 | |
| JP | 6-104503 A | 4/1994 | |
| JP | 6-507081 A | 8/1994 | |
| JP | H 7-508910 A | 10/1995 | |
| JP | 7-308323 A | 11/1995 | |
| JP | 8-24266 A | 1/1996 | |
| JP | 8-275951 A | 10/1996 | |
| JP | H 08-299351 A | 11/1996 | |
| JP | H 09-503146 A | 3/1997 | |
| JP | H 09-135553 A | 5/1997 | |
| JP | 10-295700 A | 11/1998 | |
| JP | H 11-501543 A | 2/1999 | |
| JP | H 11-128238 | 5/1999 | |
| JP | H 11-192235 A | 7/1999 | |
| JP | 11-253451 A | 9/1999 | |
| JP | 2000-041991 A | 2/2000 | |
| JP | 2000-070279 A | 3/2000 | |
| JP | 2000-210299 A | 8/2000 | |
| JP | 2000-287987 A | 10/2000 | |
| JP | 2001-029353 A | 2/2001 | |
| JP | 2001-502216 A | 2/2001 | |
| JP | 2001-309925 A | 11/2001 | |
| JP | 2002-186901 A | 7/2002 | |
| JP | 2002-263579 A | 9/2002 | |
| JP | 2002-330977 A | 11/2002 | |
| JP | 2002-542690 A | 12/2002 | |
| JP | 2003-000612 A | 1/2003 | |
| JP | 2003-510158 A | 3/2003 | |
| JP | 2003-126110 A | 5/2003 | |
| JP | 2003-310627 A | 5/2003 | |
| JP | 2003-339730 A | 12/2003 | |
| JP | 2004-147701 A | 5/2004 | |
| JP | 2005027026 A | 1/2005 | |
| JP | 2005-066316 A | 3/2005 | |
| JP | 2005-074088 A | 3/2005 | |
| JP | 2005-534451 A | 11/2005 | |
| JP | 2006-116194 A | 5/2006 | |
| JP | 2006-158525 A | 6/2006 | |
| JP | 2006-218296 A | 8/2006 | |
| JP | 2006217716 A | 8/2006 | |
| JP | 2006-288431 A | 10/2006 | |
| JP | 2008-508065 A | 3/2008 | |
| JP | 2008-119250 A | 5/2008 | |
| JP | 2008-521503 A | 6/2008 | |
| JP | 2009-511206 A | 3/2009 | |
| JP | 2010-514923 A | 5/2010 | |
| WO | WO 92/22259 A2 | 12/1992 | |
| WO | WO 93/14708 A1 | 8/1993 | |
| WO | WO 94/21183 A1 | 9/1994 | |
| WO | WO 95/09572 A1 | 4/1995 | |
| WO | WO 96/30885 A1 | 10/1996 | |
| WO | WO 98/26739 A1 | 6/1998 | |
| WO | WO 98/37815 A1 | 9/1998 | |
| WO | WO 01/54590 A1 | 8/2001 | |

(56) References Cited

FOREIGN PATENT DOCUMENTS

| | | |
|---|---|---|
| WO | WO 01/67970 A1 | 9/2001 |
| WO | WO 01/95810 A2 | 12/2001 |
| WO | WO 02/062241 A1 | 8/2002 |
| WO | WO 2004/012615 A1 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/112618 A2 | 12/2004 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/119139 A2 | 11/2006 |
| WO | WO 2006/129465 A1 | 12/2006 |
| WO | WO 2007/008710 A2 | 1/2007 |
| WO | WO 2007/040818 A1 | 4/2007 |
| WO | WO 2007/047531 A2 | 4/2007 |
| WO | WO 2007/056590 A1 | 5/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/130793 A1 | 10/2008 |
| WO | WO 2009/018406 A2 | 2/2009 |
| WO | WO 2009/027065 A1 | 3/2009 |
| WO | WO 2009/046234 A2 | 4/2009 |
| WO | WO 2009/120992 A2 | 10/2009 |
| WO | WO 2010/068783 A1 | 6/2010 |
| WO | WO 2011/008672 A2 | 1/2011 |
| WO | WO 2011/144911 A1 | 11/2011 |
| WO | WO 2013/018934 A1 | 2/2013 |
| WO | WO 2013/062978 A2 | 5/2013 |

OTHER PUBLICATIONS

International Preliminary Report on Patentability for PCT/US2011/024205, Aug. 14, 2012 (6 pages).

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the Internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gernert, eds., Plenum, New York (1995).

Campbell et al, "Thermal Imaging in Surgery," p. 19-3, in *Medical Infrared Imaging*, N. A. Diakides and J. D. Bronzino, Eds. (2008).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).

Walsh, S. J., White, R. G., "Vibrational Power Transmission in Curved Beams," Journal of Sound and Vibration, 233(3), 455-488 (2000).

U.S. Appl. No. 13/751,680, filed Jan. 28, 2013.
U.S. Appl. No. 14/136,836, filed Dec. 20, 2013.
U.S. Appl. No. 13/657,315, filed Oct. 22, 2012.
U.S. Appl. No. 13/657,553, filed Oct. 22, 2012.
U.S. Appl. No. 14/172,334, filed Feb. 4, 2014.
U.S. Appl. No. 13/804,205, filed Mar. 14, 2013.
U.S. Appl. No. 13/843,295, filed Mar. 15, 2013.
U.S. Appl. No. 13/833,706, filed Mar. 15, 2013.
European Search Report for 11705107.8, dated Jun. 25, 2013 (5 pages).

* cited by examiner

DUAL PURPOSE SURGICAL INSTRUMENT FOR CUTTING AND COAGULATING TISSUE

CROSS-REFERENCE TO RELATED APPLICATIONS

This application is a continuation application under 35 U.S.C. §120 of U.S. patent application Ser. No. 12/703,879, entitled DUAL PURPOSE SURGICAL INSTRUMENT FOR CUTTING AND COAGULATING TISSUE, filed on Feb. 11, 2010, now U.S. Pat. No. 8,486,096, the entire disclosure of which is hereby incorporated by reference herein.

BACKGROUND

The present disclosure generally relates to ultrasonic surgical systems and, more particularly, to ultrasonic systems that allow surgeons to perform cutting and coagulation of tissue.

Over the years, a variety of different types of non-ultrasonically powered cutters and shaving devices for performing surgical procedures have been developed. Some of these devices employ a rotary cutting instrument and other devices employ a reciprocating cutting member. For example, shavers are widely used in arthroscopic surgery. These devices generally consist of a power supply, a handpiece, and a single-use end effector. The end effector commonly has an inner and outer tube. The inner tube rotates relative to the outer tube and will cut tissue with its sharpened edges. The inner tube can rotate continuously or oscillate. In addition, such device may employ a suction channel that travels through the interior of the inner tube. For example, U.S. Pat. No. 4,850,354 to McGurk-Burleson, et al., discloses a non-ultrasonically powered surgical cutting instrument that comprises a rotary cutter for cutting material with a shearing action. It employs an inner cutting member which is rotatable within an outer tube. Those devices lack the ability to coagulate tissue.

U.S. Pat. No. 3,776,238 to Peyman et al. discloses an ophthalmic instrument in which tissue is cut by a chopping action set-up by the sharp end of an inner tube moving against the inner surface of the end of an outer tube. U.S. Pat. No. 5,226,910 to Kajiyama et al. discloses another surgical cutting instrument that has an inner member which moves relative to an outer member to cut tissue entering through an aperture in the outer member. Again each of those devices lack the ability to coagulate tissue.

U.S. Pat. No. 4,922,902 to Wuchinich et al. discloses a method and apparatus for endoscopic removal of tissue utilizing an ultrasonic aspirator. The device uses an ultrasonic probe which disintegrates compliant tissue and aspirates it through a narrow orifice. U.S. Pat. No. 4,634,420 to Spinosa et al. discloses an apparatus and method for removing tissue from an animal and includes an elongated instrument having a needle or probe, which is vibrated at an ultrasonic frequency in the lateral direction. The ultrasonic movement of the needle breaks-up the tissue into fragments. Pieces of tissue can be removed from the area of treatment by aspiration through a conduit in the needle. U.S. Pat. No. 3,805,787 to Banko discloses yet another ultrasonic instrument that has a probe that is shielded to narrow the beam of ultrasonic energy radiated from the tip of the probe. In one embodiment the shield extends past the free-end of the probe to prevent the probe from coming into contact with the tissue. U.S. Pat. No. 5,213,569 to Davis discloses a phaco-emulsification needle which focuses the ultrasonic energy. The focusing surfaces can be beveled, curved or faceted. U.S. Pat. No. 6,984,220 to Wuchinich and U.S. Patent Publication No. US 2005/0177184 to Easley disclose ultrasonic tissue dissection systems that provide combined longitudinal and torsional motion through the use of longitudinal-torsional resonators. U.S Patent Publication no. US 2006/0030797 A1 to Zhou et al. discloses an orthopedic surgical device that has a driving motor for driving an ultrasound transducer and horn. An adapter is provided between the driving motor and transducer for supplying ultrasonic energy signals to the transducer.

While the use of ultrasonically powered surgical instruments provide several advantages over traditional mechanically powered saws, drills, and other instruments, temperature rise in bone and adjacent tissue due to frictional heating at the bone/tissue interface can still be a significant problem. Current arthroscopic surgical tools include punches, reciprocating shavers and radio frequency (RF) devices. Mechanical devices such as punches and shavers create minimal tissue damage, but can sometimes leave behind ragged cut lines, which are undesirable. RF devices can create smoother cut lines and also ablate large volumes of soft tissue; however, they tend to create more tissue damage than mechanical means. Thus, a device which could provide increased cutting precision while forming smooth cutting surfaces without creating excessive tissue damage would be desirable.

It would be desirable to provide an ultrasonic surgical instrument that overcomes some of the deficiencies of current instruments. The ultrasonic surgical instruments described herein overcome many of those deficiencies.

The foregoing discussion is intended only to illustrate some of the shortcomings present in the field of the invention at the time, and should not be taken as a disavowal of claim scope.

SUMMARY

In one general aspect, various embodiments are directed to an ultrasonic surgical instrument that may include a housing that has a motor therein. A cutting blade may be coupled to the motor and be supported for selective rotational travel relative to the housing. At least one ultrasonic transducer may be supported by the housing. An ultrasonic blade may protrude from the at least one ultrasonic transducer such that the ultrasonic blade extends coaxially through a lumen in the cutting blade to protrude through a distal end thereof.

In connection with another general aspect of the present invention, there is provided an ultrasonic surgical instrument that may include a housing that supports at least one ultrasonic transducer therein. A substantially hollow ultrasonic blade may be coupled to the at least one ultrasonic transducer. A cutting blade may extend through the substantially hollow ultrasonic blade. The cutting blade may have a tissue cutting distal end that protrudes outward from a distal end of the substantially hollow ultrasonic blade. A motor may be coupled to the cutting blade for rotating the cutting blade within the substantially hollow ultrasonic blade.

In connection with still another general aspect of the present invention, there is provided an ultrasonic surgical instrument that may include a housing that supports a motor. a cutting blade may be coupled to the motor and be supported for selective rotational travel relative to the housing. A least one ultrasonic transducer may be supported by the housing and have an ultrasonic blade protruding therefrom. The ultrasonic blade may be substantially parallel to the cutting blade.

FIGURES

The features of various embodiments are set forth with particularity in the appended claims. The various embodiments, however, both as to organization and methods of operation, together with further objects and advantages thereof, may best be understood by reference to the following description, taken in conjunction with the accompanying drawings as follows.

DESCRIPTION

Figure 1:
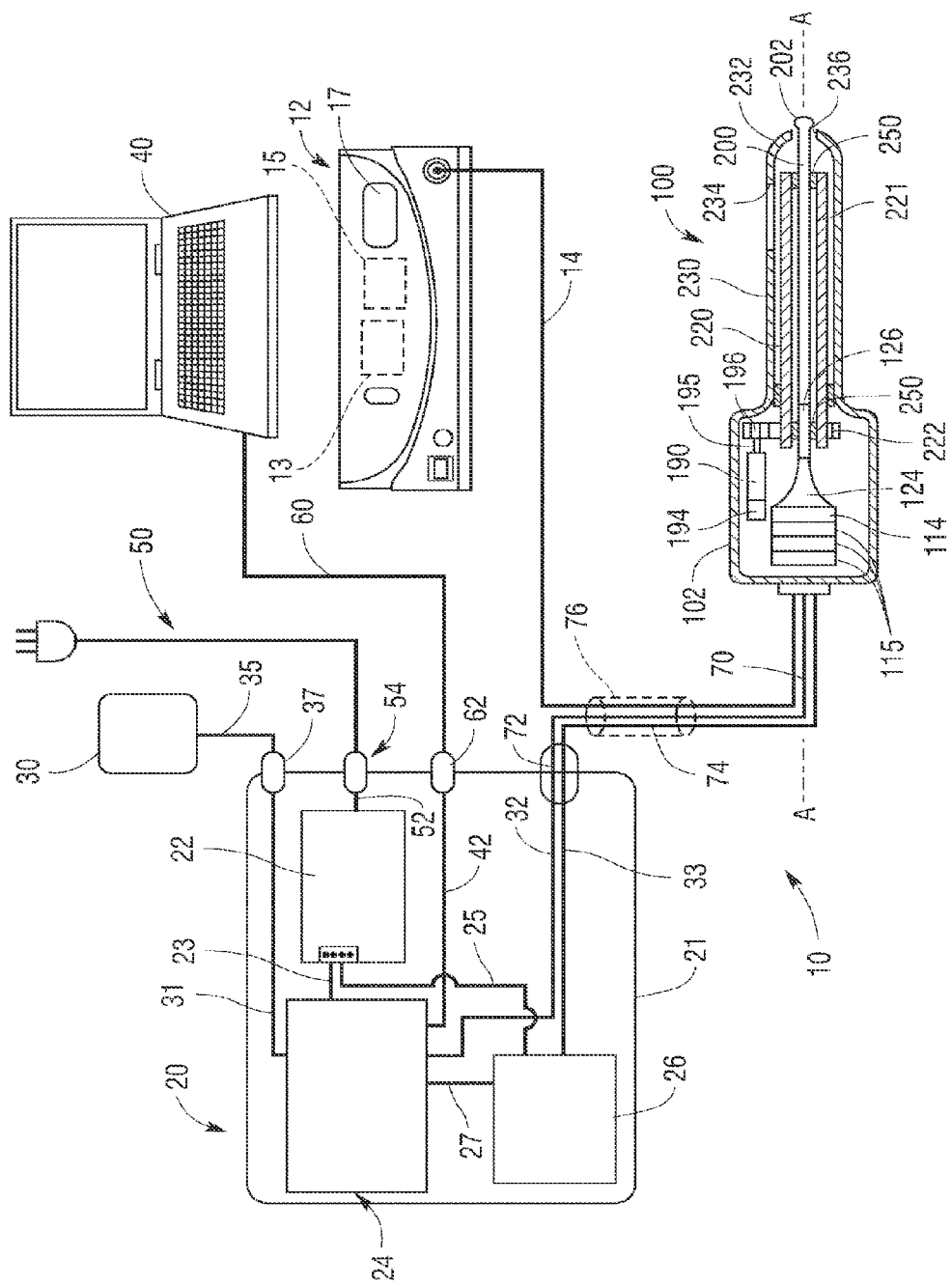
FIG. 1 is a schematic view of a surgical control system embodiment of the present invention in use with a non-limiting surgical instrument embodiment of the present invention.

The owner of the present application also owns the following U.S. patent applications that were filed on even date herewith and which are herein incorporated by reference in their respective entireties:

U.S. patent application Ser. No. 12/703,860, entitled ULTRASONICALLY POWERED SURGICAL INSTRUMENTS WITH ROTATING CUTTING IMPLEMENT, now U.S. Pat. No. 8,531,064;

U.S. patent application Ser. No. 12/703,864, entitled METHODS OF USING ULTRASONICALLY POWERED SURGICAL INSTRUMENTS WITH ROTATABLE CUTTING IMPLEMENTS, now U.S. Pat. No. 8,323,302;

U.S. patent application Ser. No. 12/703,866, entitled SEAL ARRANGEMENTS FOR ULTRASONICALLY POWERED SURGICAL INSTRUMENTS, now U.S. Patent Application Publication No. 2011/0196398;

U.S. patent application Ser. No. 12/703,870, entitled ULTRASONIC SURGICAL INSTRUMENTS WITH ROTATABLE BLADE AND HOLLOW SHEATH ARRANGEMENTS, now U.S. Patent Application Publication No. 2011/0196399;

U.S. patent application Ser. No. 12/703,875, entitled ROTATABLE CUTTING IMPLEMENT ARRANGEMENTS FOR ULTRASONIC SURGICAL INSTRUMENTS, now U.S. Pat. No. 8,469,981;

U.S. patent application Ser. No. 12/703,877, entitled ULTRASONIC SURGICAL INSTRUMENTS WITH PARTIALLY ROTATING BLADE AND FIXED PAD ARRANGEMENT, now U.S. Pat. No. 8,382,782;

U.S. patent application Ser. No. 12/703,885, entitled OUTER SHEATH AND BLADE ARRANGEMENTS FOR ULTRASONIC SURGICAL INSTRUMENTS, now U.S. Pat. No. 8,579,928;

U.S. patent application Ser. No. 12/703,893, entitled ULTRASONIC SURGICAL INSTRUMENTS WITH MOVING CUTTING IMPLEMENT, now U.S. Patent Application Publication No. 2011/0196404; and U.S. patent application Ser. No. 12/703,899, entitled ULTRASONIC SURGICAL INSTRUMENT WITH COMB-LIKE TISSUE TRIMMING DEVICE, now U.S. Pat. No. 8,419,759.

Various embodiments are directed to apparatuses, systems, and methods for the treatment of tissue Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Various embodiments are directed to improved ultrasonic surgical systems and instruments configured for effecting tissue dissecting, cutting, and/or coagulation during surgical procedures as well as the cutting implements employed thereby. In one embodiment, an ultrasonic surgical instrument apparatus is configured for use in open surgical procedures, but has applications in other types of surgery, such as arthroscopic, laparoscopic, endoscopic, and robotic-assisted procedures. Versatile use is facilitated by selective use of ultrasonic energy and the selective rotation of the cutting/coagulation implement and/or protective sheaths.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

FIG. 1 illustrates in schematic form one embodiment of a surgical control system 10 of the present invention that may be employed to control various surgical instrument embodiments of the present invention. For example, the surgical control system 10 may include an ultrasonic generator 12 for supplying ultrasonic control signals to an ultrasonic surgical instrument 100. The ultrasonic generator 12 may be connected by a cable 14 to an ultrasonic transducer assembly 114 that is non-rotatably supported within a housing 102 of the ultrasonic surgical instrument 100. In one embodiment, the system 10 may further include a motor control system 20 that includes a conventional power supply 22 that is coupled to a control module 24 by cable 23 to supply, for example, 24 VDC thereto. The motor control module 24 may comprise a control module manufactured by National Instruments of Austin, Tex. under Model No. NI cRIO-9073. However, other conventional motor control modules may be employed. The power supply 22 may be coupled to a motor drive 26 by cable 25 to also supply 24 VDC thereto. The motor drive 26 may comprise a motor drive manufactured by National Instruments. However, other conventional motor drives may be employed. Control module 24 may also be coupled to the motor drive 26 by cable 27 for supplying power thereto. A conventional foot pedal 30 or other control switch arrangement may be attached to the control module 24 by a cable 31. As will be discussed in further detail below, the ultrasonic surgical instrument 100 may include a motor 190 that has an encoder 194 associated therewith. The motor 190 may comprise a motor manufactured by National Instruments under Model No. CTP12ELF10MAA00. The encoder 194 may comprise an encoder manufactured by U.S. Digital of Vancouver, Wash. under Model No. 197-I-D-D-B. However, other conventional motors and conventional encoders may be used. The encoder 194 may be coupled to the motor control module 24 by an encoder cable 32 and the motor 190 may be coupled to the motor drive 26 by cable 33. The surgical system 10 may also include a computer 40 that may communicate by Ethernet cable 42 with the motor control module 24.

As can also be seen in FIG. 1, the motor control system 20 may be housed in an enclosure 21. To facilitate easy portability of the system, various components may be attached to the motor control system 20 by removable cable connectors. For example, foot pedal switch 30 may be attached to a detachable cable connector 37 by cable 35 to facilitate quick attachment of the foot pedal to the control system 20. A/C power may be supplied to the power supply 22 by a conventional plug/cable 50 that is attached to a detachable cable connector 54 that is attached to cable 52. The computer 40 may have a cable 60 that is attached to detachable cable connector 62 that is coupled to cable 42. The encoder 194 may have an encoder cable 70 that is attached to a detachable connector 72. Likewise, the motor 190 may have a cable 74 that is attached to the detachable connector 72. The detachable connector 72 may be attached to the control module 24 by cable 32 and the connector 72 may be attached to the motor drive 26 by cable 33. Thus, cable connector 72 serves to couple the encoder 194 to the control module 24 and the motor 190 to the motor drive 26. The cables 70 and 74 may be housed in a common sheath 76.

In various embodiments, the ultrasonic generator 12 may include an ultrasonic generator module 13 and a signal generator module 15. See FIG. 1. The ultrasonic generator module 13 and/or the signal generator module 15 each may be integrated with the ultrasonic generator 12 or may be provided as a separate circuit module electrically coupled to the ultrasonic generator 12 (shown in phantom to illustrate this option). In one embodiment, the signal generator module 15 may be formed integrally with the ultrasonic generator module 13. The ultrasonic generator 12 may comprise an input device 17 located on a front panel of the generator 12 console. The input device 17 may comprise any suitable device that generates signals suitable for programming the operation of the generator 12 in a known manner. Still with reference to FIG. 1, the cable 14 may comprise multiple electrical conductors for the application of electrical energy to positive (+) and negative (−) electrodes of an ultrasonic transducer assembly 114. In alternative embodiments, the ultrasonic drive module and/or the motor drive module may be supported within the surgical instrument 100.

Various forms of ultrasonic generators, ultrasonic generator modules and signal generator modules are known. For example, such devices are disclosed in commonly owned U.S. patent application Ser. No. 12/503,770, now U.S. Pat. No. 8,461,744, entitled Rotating Transducer Mount For Ultrasonic Surgical Instruments, filed Jul. 15, 2009, which is herein incorporated by reference in its entirety. Other such devices are disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

In various embodiments, the housing 102 may be provided in two or more sections that are attached together by fasteners such as screws, snap features, etc. and may be fabricated from, for example, plastics such as polycarbonate, polyetherimide (GE Ultem®) or metals such as aluminum, titanium or stainless steel. As indicated above, the housing 102 non-rotatably supports a piezoelectric ultrasonic transducer assembly 114 for converting electrical energy to mechanical energy that results in longitudinal vibrational motion of the ends of the transducer assembly 114. The ultrasonic transducer assembly 114 may comprise at least one and preferably a stack of, for example, four to eight ceramic piezoelectric elements 115 with a motion null point located at some point along the stack. The ultrasonic transducer assembly 114 may further include an ultrasonic horn 124 that is attached at the null point on one side and to a coupler 126 on the other side. An ultrasonic blade 200 that may be fabricated from, for example, titanium may be fixed to the coupler 126. In alternative embodiments, the ultrasonic blade 200 is integrally formed with the ultrasonic horn 124. In either case, the ultrasonic blade 200 will vibrate in the longitudinal direction at an ultrasonic frequency rate with the ultrasonic transducer assembly 114. The ends of the ultrasonic transducer assembly 114 achieve maximum motion with a portion of the stack constituting a motionless node, when the ultrasonic transducer assembly 114 is driven at maximum current at the transducer's resonant frequency. However, the current providing the maximum motion will vary with each instrument and is a value stored in the non-volatile memory of the instrument so the system can use it.

The parts of the ultrasonic instrument 100 may be designed such that the combination will oscillate at the same resonant frequency. In particular, the elements may be tuned such that the resulting length of each such element is one-half wavelength or a multiple thereof. Longitudinal back and forth motion is amplified as the diameter closer to the ultrasonic blade 200 of the acoustical mounting horn 124 decreases. This phenomenon is greatest at the node and essentially non-existent when the diameteral change is made at an anti-node. Thus, the ultrasonic horn 124, as well as the blade/coupler, may be shaped and dimensioned so as to amplify blade motion and provide ultrasonic vibration in resonance with the rest of the acoustic system, which produces the maximum back and forth motion of the end of the acoustical mounting horn 124 close to the ultrasonic blade 200. Motions of approximately 10 microns may be achieved at the piezoelectric elements 115. Motions of approximately 20-25 microns may be achieved at the end of the acoustical horn 124 and motions of approximately 40-100 microns may be achieved at the end of the ultrasonic blade 200.

When power is applied to the ultrasonic instrument 100 by operation of the foot pedal 30 or other switch arrangement, the ultrasonic generator 12 may, for example, cause the ultrasonic blade 200 to vibrate longitudinally at approximately 55.5 kHz, and the amount of longitudinal movement will vary proportionately with the amount of driving power (current) applied, as adjustably selected by the user. When relatively high power is applied, the ultrasonic blade 200 may be designed to move longitudinally in the range of about 40 to 100 microns at the ultrasonic vibrational rate. Such ultrasonic vibration of the blade 200 will generate heat as the blade contacts tissue, i.e., the acceleration of the ultrasonic blade 200 through the tissue converts the mechanical energy of the moving ultrasonic blade 200 to thermal energy in a very narrow and localized area. This localized heat creates a narrow zone of coagulation, which will reduce or eliminate bleeding in small vessels, such as those less than one millimeter in diameter. The cutting efficiency of the ultrasonic blade 200, as well as the degree of hemostasis, will vary with the level of driving power applied, the cutting rate or force applied by the surgeon to the blade, the nature of the tissue type and the vascularity of the tissue.

As indicated above, the surgical instrument 100 may further include a motor 190 which is employed to apply rotational motion to a tissue cutting blade 220 that is coaxially aligned with the ultrasonic blade 200. More particularly, the tissue cutting blade 220 has an axial lumen 221 therethrough through which the ultrasonic blade 200 extends. The tissue cutting blade 220 may be fabricated from, for example, stainless steel. In various embodiments, one or more seals 250 of the type described in co-pending U.S. patent application Ser. No. 12/703,866, entitled SEAL ARRANGEMENTS FOR ULTRASONICALLY POWERED SURGICAL INSTRUMENTS, now U.S. Patent Application Publication No. 2011/0196398, which has been herein incorporated by reference inn its entirety may be employed. However, other seal arrangements could also be employed. The motor 190 may comprise, for example, a conventional stepper motor. When used with an encoder 194, the encoder 194 converts the mechanical rotation of the motor shaft 192 into electrical pulses that provide speed and other motor control information to the control module 24.

Figure 2:
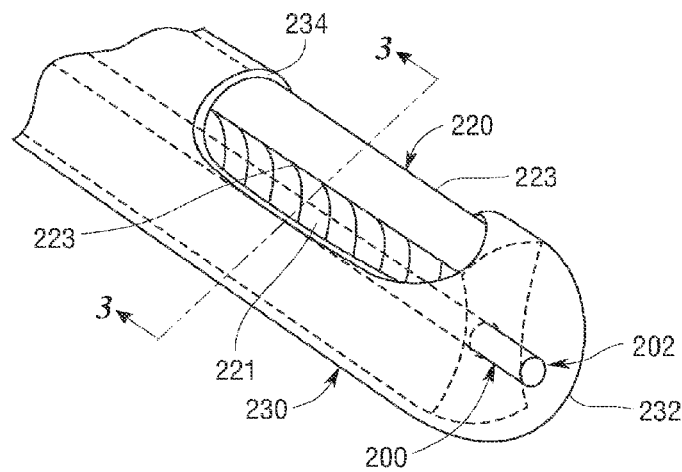
FIG. 2 is a partial perspective view of a portion of the outer sheath and blade arrangement of the surgical instrument depicted in FIG. 1.
Figure 3:
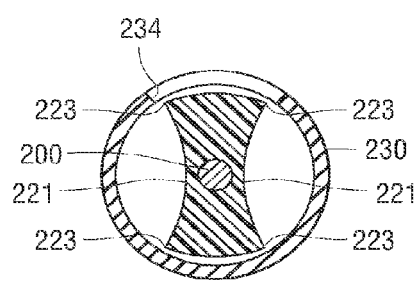
FIG. 3 is a cross-sectional view of the outer sheath and blade arrangement of FIG. 2 taken along line 3-3 in FIG. 2.
Figure 5:
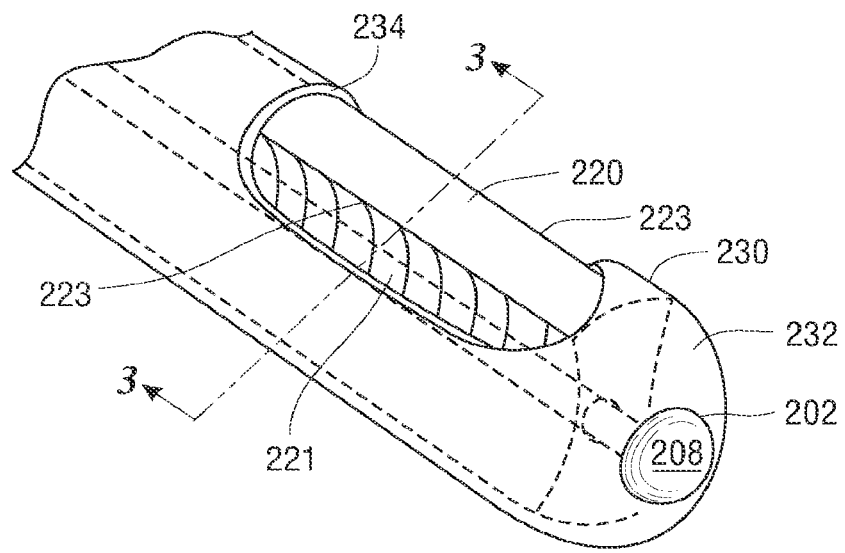
FIG. 5 is a partial perspective view of another non-limiting outer sheath and blade arrangement of the present invention.
Figure 6:
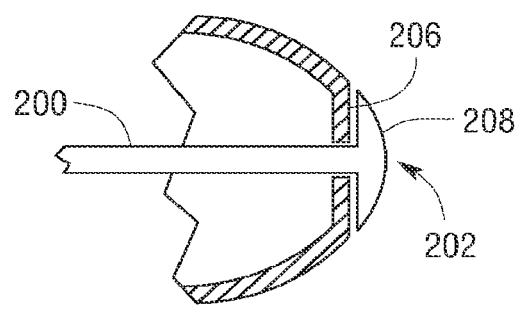
FIG. 6 is a partial cross-sectional view of the outer sheath and ultrasonic blade of the arrangement depicted in FIG. 5.

As can also be seen in FIG. 1, a drive gear 196 may be attached to the motor shaft 195. The drive gear 196 may be supported in meshing engagement with a driven gear 222 that may be attached to the tissue cutting blade 220. Such arrangement serves to facilitate the rotation of the tissue cutting blade 220 about the longitudinal axis A-A when the motor 190 is powered. The tissue cutting blade 220 may also be rotatably supported within an outer sheath 230 by one or more bearings 224. The outer sheath 230 may be fixed to the housing 102 and have a substantially blunt distal end 232. A hole or opening 236 may be provided through the blunt distal end 232 to enable at least a portion of a distal end 202 of the ultrasonic blade 200 to protrude therethrough. See FIGS. 1 and 2. The distal end 202 of the ultrasonic blade 200 may have a ball-like shape as shown in FIGS. 1-3 or, in other embodiments for example, the distal end 202 may have a somewhat flattened portion 206 with an arcuate or rounded distal surface 208 as shown in FIGS. 5 and 6.

Figure 4:
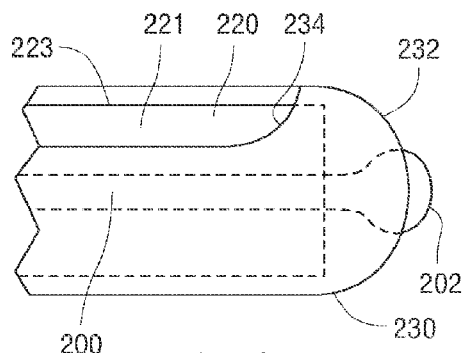
FIG. 4 is a partial side elevational view of the outer sheath and blade arrangement of FIGS. 2 and 3.

The tissue cutting blade 220 may have various configurations. In the embodiment depicted in FIGS. 2-4, the tissue cutting blade 220 has two opposed arcuate portions 221 that serve to form four tissue cutting edges 223. As can be seen in FIG. 2, one portion of the tissue cutting blade 220 is exposed through the distal tissue opening 234. Because in this embodiment, the tissue cutting blade 220 is not ultrasonically active, the blade 220 may be fabricated from a material that will facilitate holding sharp edges. For example, the tissue cutting blade 220 may be fabricated from, for example, stainless steel or other suitable materials. In use, the surgeon could use the portion of the rotating tissue cutting blade 220 that is exposed through the distal tissue cutting opening 234 to cut tissue and then activate the ultrasonic blade 200 when it is needed for coagulation purposes. The surgeon would simply contact the target tissue with the exposed portion of the distal end 202 of the ultrasonic blade 200 while activating the ultrasonic transducer assembly 114.

Figure 7:
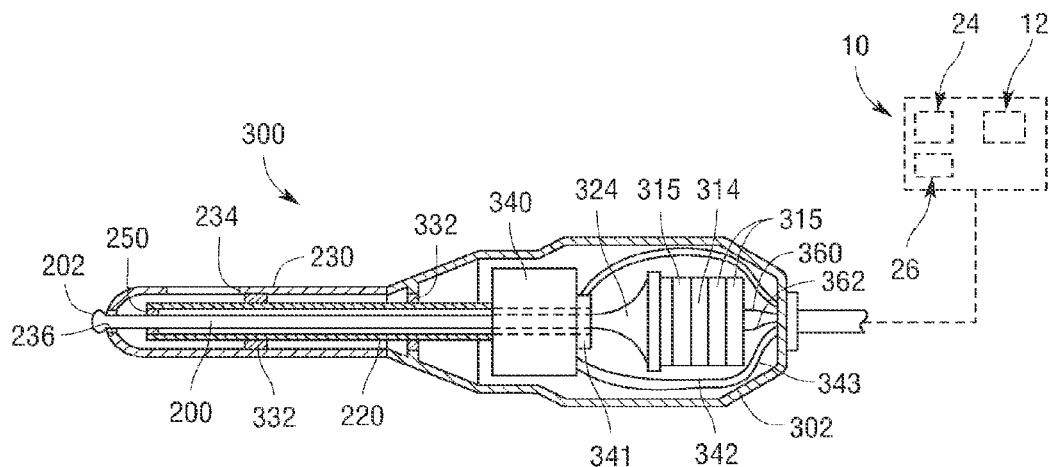
FIG. 7 is a cross-sectional view of another non-limiting surgical instrument embodiment of the present invention.

FIG. 7 illustrates another surgical instrument 300 of the present invention. The surgical instrument 300 includes a housing 302 that may house a transducer assembly 314 that includes an ultrasonic horn 324. The ultrasonic transducer assembly 314 may comprise at least one and preferably a stack of, for example, four to eight ceramic piezoelectric elements 315 with a motion null point located at some point along the stack. In this embodiment, the transducer assembly 314 is non-rotatably supported within the housing 302. Power may be transmitted to the ultrasonic transducer assembly 314 by conductors 360, 362 which are coupled to the ultrasonic generator 12 in the control system 10. The surgical instrument 300 may include a control arrangement of the type described above and be used in the various modes described above. The motor 340 may have an encoder 341 associated therewith that communicates with the control module 24 as was described above. The motor 340 may receive power from the motor drive 26 through conductors 342, 343 that comprise motor cable 74 that extends through the common sheath 76.

An ultrasonic blade 200 of the types and construction described above may be attached to the ultrasonic horn 324 in a manner described above and may extend through a bore 342 in a motor 340 that is mounted within the housing 302. In alternative embodiments, however, the ultrasonic blade 200 may be integrally formed with the ultrasonic horn 324. A tissue cutting blade 220 of the various types and constructions described above may be attached to a rotatable portion/shaft of the motor 340. For example, those motors manufactured by National Instruments may be used. However, other motors may also be successfully employed. The tissue cutting blade 220 may coaxially extend through an outer sheath 230 that is attached to the housing 302. The outer sheath 230 may be fabricated from, for example, aluminum, titanium, aluminum alloys, steels, ceramics, etc. The tissue cutting blade 220 may be rotatably supported by one or more bearings 332 mounted between the housing 302 and/or the outer sheath 230. One or more seals 250 of the type and construction described in one of the aforementioned patent applications or others may be mounted between the ultrasonic blade 200 and the tissue cutting blade 220. The ultrasonic horn 324 may be coupled to the proximal end of the ultrasonic blade 200 in the manner described above. In use, the surgeon may use the portion of the rotating tissue cutting blade 220 that is exposed through the distal tissue cutting opening 234 in the outer sheath 230 to cut tissue and then activate the ultrasonic blade 200 when it is needed for coagulation purposes. The surgeon would simply contact the target tissue with the distal end 202 of the ultrasonic blade 200 while activating the ultrasonic transducer assembly 314. It will be understood that the instrument 300 may be used in a tissue cutting rotation mode, an ultrasonic mode, or tissue cutting and ultrasonic mode ("duel mode").

Figure 8:
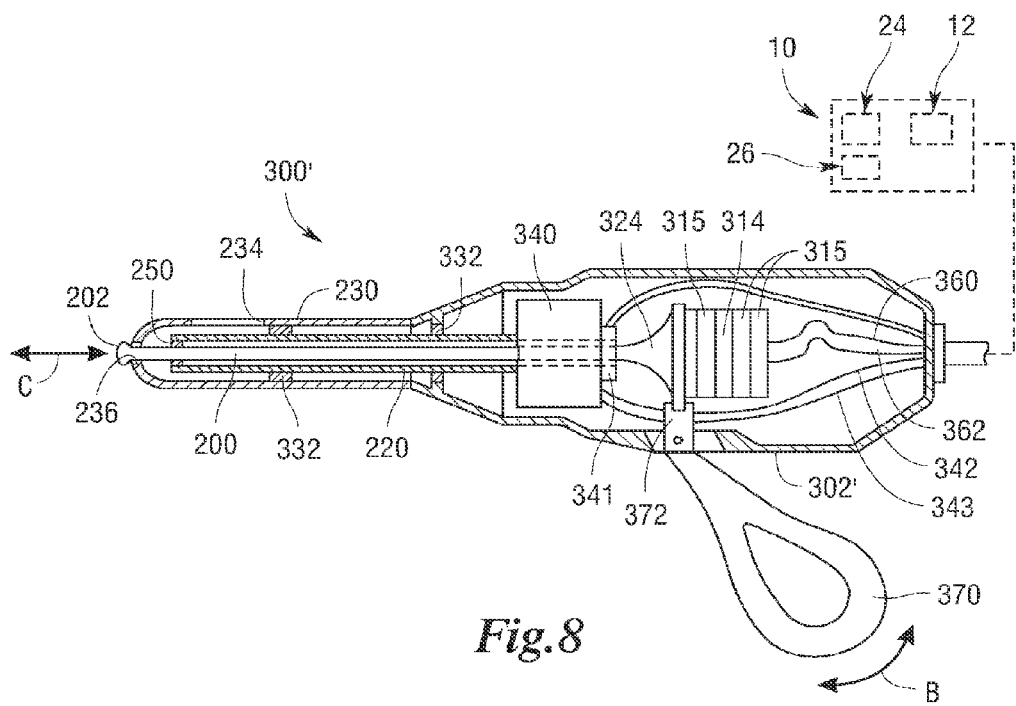
FIG. 8 is a cross-sectional view of another non-limiting surgical instrument embodiment of the present invention.

FIG. 8 illustrates an alternative surgical instrument 300' that is substantially identical to surgical instrument 300 described above, except for the following differences. As can be seen in FIG. 8, the ultrasonic transducer assembly 314 and the ultrasonic blade 200 are capable of being moved axially by a trigger 370 that is pivotally coupled to the housing 302'. In various embodiments, the trigger 370 may have a yoke 372 that is configured to engage a portion of the transducer assembly 314 such that when the trigger 370 is pivoted (arrow "B"), the ultrasonic transducer assembly 314, and ultrasonic blade 200 move axially along axis A-A (represented by arrow "C"). This "gross" axial motion is distinguishable from ultrasonic axial motion achieved when the ultrasonic transducer assembly 314 is powered.

Figure 9:
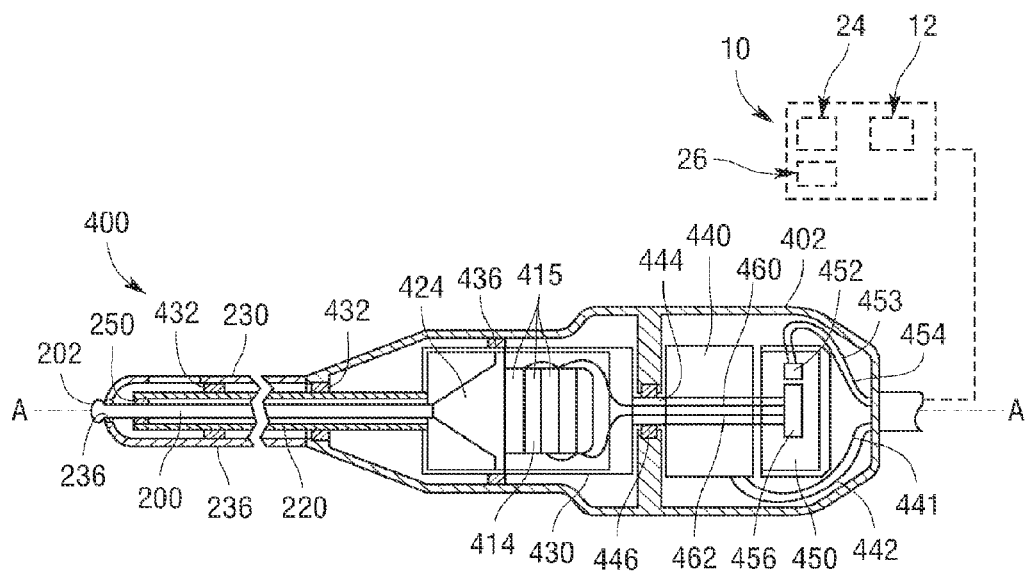
FIG. 9 is a cross-sectional view of another non-limiting surgical instrument embodiment of the present invention.

FIG. 9 illustrates another surgical instrument 400 of the present invention. The surgical instrument 400 includes a housing 402 that may house an ultrasonic transducer assembly 414 that includes an ultrasonic horn 424. The ultrasonic transducer assembly 414 may comprise at least one and preferably a stack of, for example, four to eight PZT-8 (Lead Zirconium Titanate) ceramic piezoelectric elements 415 with a motion null point located at some point along the stack. In this embodiment, the ultrasonic transducer assembly 414 is attached to a transducer housing 430 that is rotatably supported within the housing 402 by a distal bearing 436. The ultrasonic transducer assembly 414 may be substantially ultrasonically insulated from the transducer housing 430 by, for example, epdm elastomeric materials or by a flange placed at a Node and damped by a dampening member such that ultrasonic motion from the ultrasonic transducer assembly 414 is not passed to the transducer housing. A tissue cutting blade 220 of the various types and constructions described above may be attached to the transducer housing 430 for rotatable travel therewith. The tissue cutting blade 220 may coaxially extend through an outer sheath 230 that is attached to the housing 402. The tissue cutting blade 220 may be rotatably supported by one or more bearings 432 mounted between the housing 402 and/or the outer sheath 230. One or more seals 250 may be mounted between the ultrasonic blade 200 and the tissue cutting blade 200. The ultrasonic horn 424 may be coupled to the proximal end of the ultrasonic blade 200 in the manner described above. In alternative embodiments, the ultrasonic blade 200 may be integrally formed with the ultrasonic horn 424.

This embodiment may include a conventional stepper motor 440. The motor 440 may have an encoder associated therewith that communicates with the control module 24 as was described above. The motor 440 may receive power from the motor drive 26 through conductors 441, 442 that comprise motor cable 74 that extends through the common sheath 76. The motor 440 may have a hollow motor shaft 444 attached thereto that extends through a slip ring assembly 450. The hollow motor shaft 444 may be rotatably supported within the housing 402 by a proximal bearing 446.

The slip ring assembly 450 may be fixed (i.e., non-rotatable) within the housing 402 and may include a fixed outer contact 452 that is coupled to conductors 453, 454 that form generator cable 14 as was described above. An inner contact 456 may be mounted on the rotatable hollow drive shaft 444 such that it is in electrical contact or communication with outer contact 452. Conductors 453, 454 are attached to the inner contact 456 and extend through the hollow motor shaft 444 to be coupled to the ultrasonic transducer assembly 414. In various embodiments, to facilitate ease of assembly and also acoustically isolate the motor 440 from the ultrasonic transducer assembly 414, the hollow motor shaft 444 may be detachably coupled to the transducer 430 by one of the various coupling assemblies disclosed in U.S. patent application Ser. No. 12/703,860, entitled ULTRASONICALLY POWERED SURGICAL INSTRUMENTS WITH ROTATING CUTTING IMPLEMENT, now U.S. Pat. No. 8,531,064, the disclosure of which has been herein incorporated by reference in its entirety.

When power is supplied to the motor 440, the drive shaft 444 rotates about axis A-A which also causes the transducer housing 430 to rotate about axis A-A. Because ultrasonic transducer assembly 414 and the tissue cutting blade 220 are attached to the transducer housing 430, they, too, rotate about axis A-A. When the clinician desires to power the ultrasonic transducer assembly 414, power is supplied from the ultrasonic generator 12 to the fixed contact 452 in the slip ring assembly 450. Power is transmitted to the ultrasonic transducer assembly 414 by virtue of rotational sliding contact or electrical communication between the inner contact 456 and the fixed contact 452. Those signals are transmitted to the ultrasonic transducer assembly 414 by conductors 460, 462. The surgical instrument 400 may include a control arrangement of the type described above and be used in the various modes described above. It will be understood that the instrument 400 may be used in rotation mode, ultrasonic mode, or rotation and ultrasonic mode ("duel mode").

Figure 10:
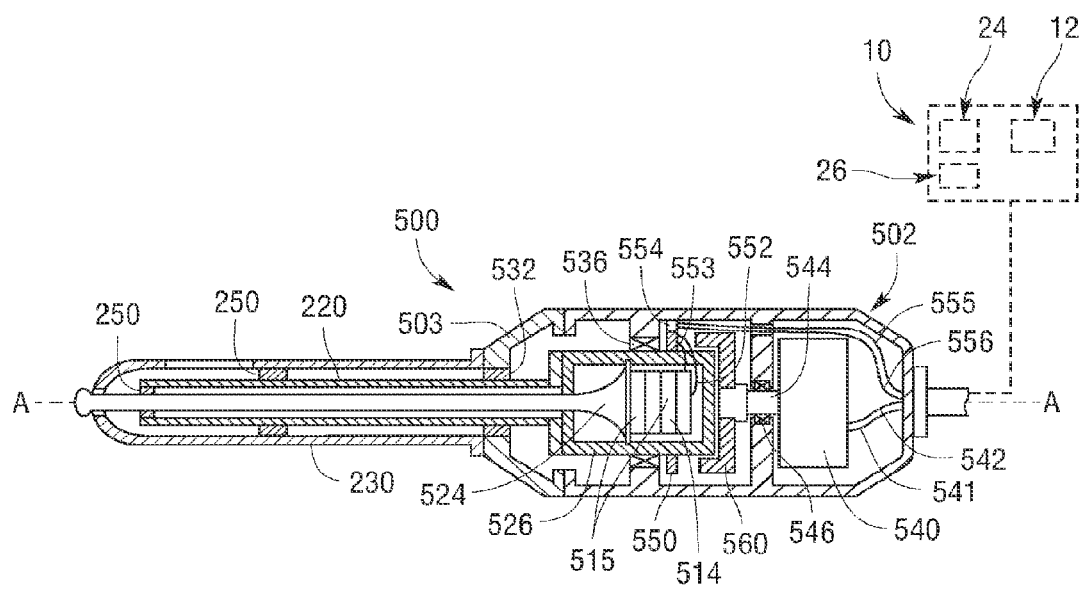
FIG. 10 is a cross-sectional view of another non-limiting surgical instrument embodiment of the present invention.

FIG. 10 illustrates another surgical instrument 500 of the present invention. The surgical instrument 500 includes a housing 502 that may house an ultrasonic transducer assembly 514 that includes an ultrasonic horn 524. The ultrasonic transducer assembly 514 may comprise at least one and preferably a stack of, for example, four to eight PZT-8 (Lead Zirconium Titanate) ceramic piezoelectric elements 515 with a motion null point located at some point along the stack. In this embodiment, the ultrasonic transducer assembly 514 is contained within a sealed transducer chamber 526 that is rotatably supported within the housing 502 by a distal bearing 536. In various embodiments, the sealed transducer chamber 526 may be fabricated from magnetic material such as, for example, iron, rare earth magnetic materials, etc. A tissue cutting blade 220 of the various types and constructions described above may be attached to the transducer chamber 526 for rotatable travel therewith. The tissue cutting blade 220 may coaxially extend through an outer sheath 230 that is attached to the housing 502. The outer sheath 230 may be fabricated from, for example, aluminum, titanium, aluminum alloys, steels, ceramics, etc. The tissue cutting blade 220 may be rotatably supported by one or more bearings 532 mounted between a nosepiece portion 503 of the housing 502 and/or the outer sheath 230. One or more seals 250 may be mounted between the ultrasonic blade 200 and the tissue cutting blade 220. The ultrasonic horn 524 may be coupled to the proximal end of the ultrasonic blade 200 in the manner described above. In alternative embodiments, the ultrasonic blade 200 may be integrally formed with the ultrasonic horn 524.

This embodiment includes a motor 540 that may comprise a stepper motor of the type and construction described above. The motor 540 may have an encoder associated therewith that communicates with the control module 24 as was described above. The motor 540 may receive power from the motor drive 26 through conductors 541, 542 that comprise motor cable 74 that extends through the common sheath 76 (FIG. 1). The motor 540 has a motor shaft 544 attached thereto that is coupled to a magnetic yoke 560 which is magnetically coupled to the transducer chamber 526. The motor shaft 544 may be rotatably supported within the housing 502 by a proximal bearing 546.

A movable contact 550 may be fixed to the sealed transducer chamber 526 and is coupled to the transducer assembly 514 by conductors 552 and 553. A fixed outer contact 554 may be attached to the housing 502 and is coupled to conductors 555, 556 that form generator cable 14 as was described above. When power is supplied to the motor 540, the motor shaft 544 rotates about axis A-A which also causes the transducer chamber 526 to rotate about axis A-A. Because ultrasonic transducer assembly 514 and the tissue cutting blade 220 are attached to the transducer chamber 526, they, too, rotate about axis A-A. When the clinician desires to power the ultrasonic transducer assembly 514, power is supplied from the ultrasonic generator 12 to the fixed contact 554. Power is transmitted to the ultrasonic transducer assembly 514 by virtue of rotational sliding contact or electrical communication between the fixed contact 554 and the movable contact 550. Those signals are transmitted to the ultrasonic transducer assembly 514 by conductors 553, 554. The surgical instrument 500 may include a control arrangement of the type described above and be used in the various modes described above. It will be understood that the instrument 500 may be used in rotation mode, ultrasonic mode, or rotation and ultrasonic mode ("duel mode").

Figure 11:
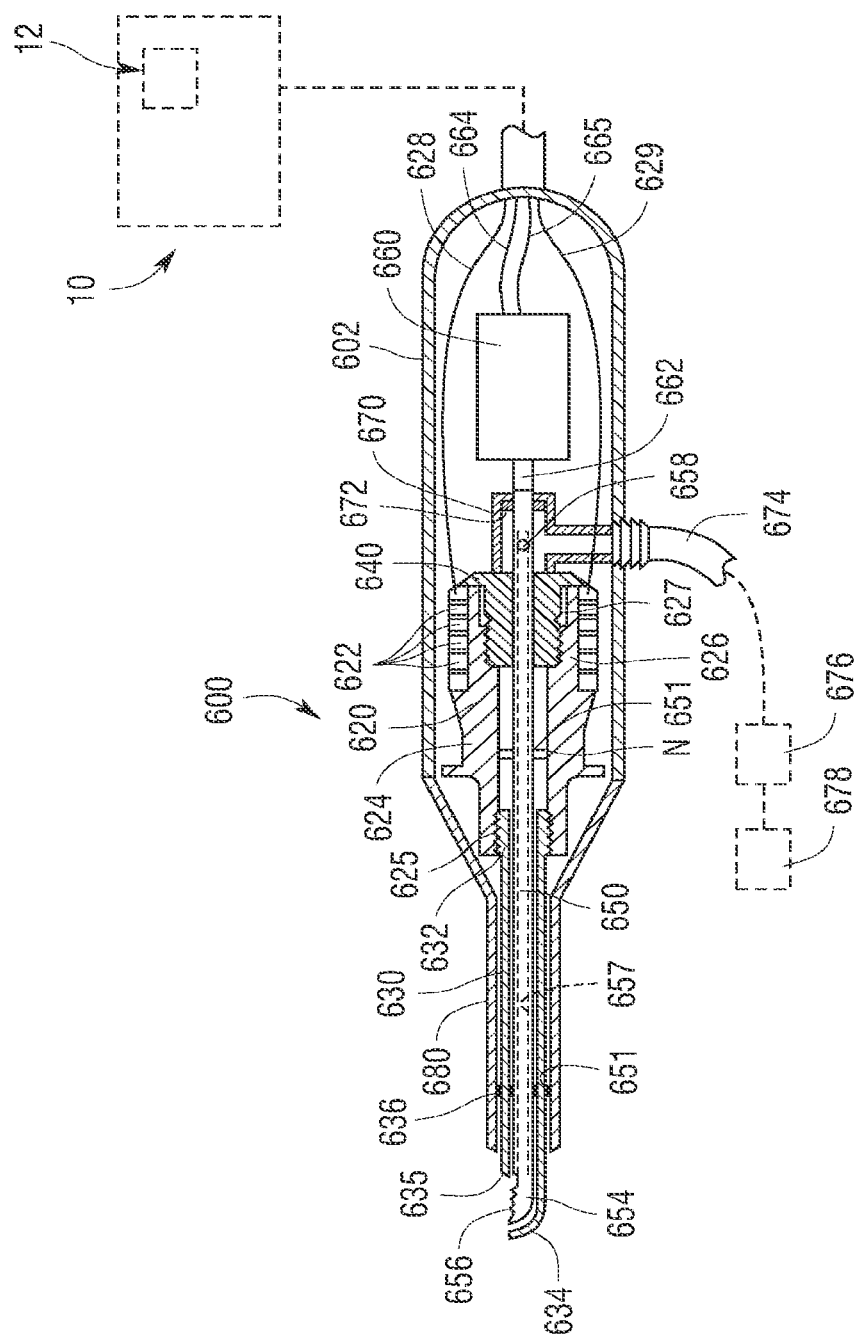
FIG. 11 is a cross-sectional view of another non-limiting surgical instrument embodiment of the present invention.
Figure 12:
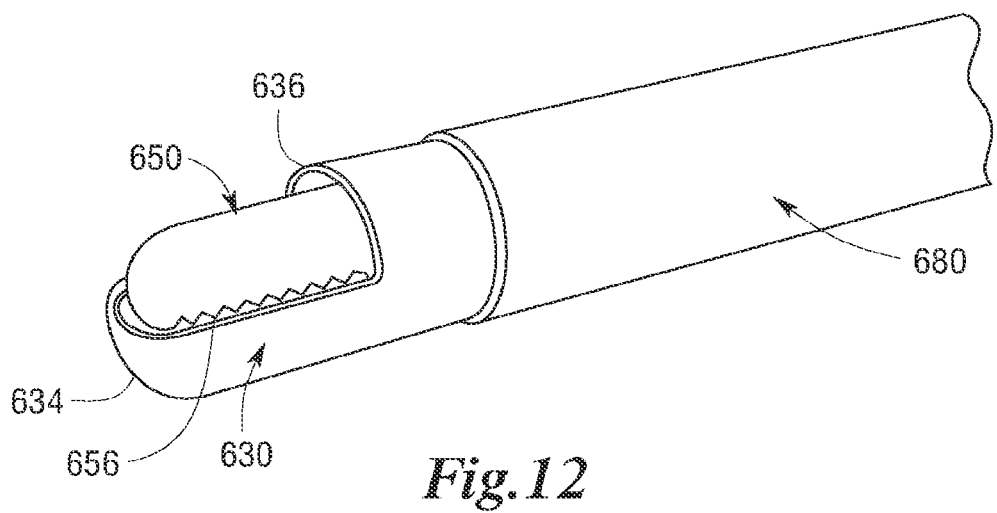
FIG. 12 is a perspective view of a portion of the outer sheath and blade arrangement employed by the surgical instrument embodiment of FIG. 11.

FIGS. 11 and 12 illustrate another surgical instrument 600 of the present invention. The surgical instrument 600 includes a housing 602 that may support a hollow transducer housing 620. The hollow transducer housing 620 may support a plurality of (e.g., four to eight) piezoceramic elements 622 and may have an ultrasonic horn portion 624 integrally formed therewith. A series of internal threads 625 may be formed on the distal end portion of the horn portion 624 for attachment to a hollow ultrasonic blade 630. Ultrasonic blade 630 may be fabricated from, for example, aluminum, titanium, aluminum alloys, steels, ceramics, etc. and have a threaded proximal end 632 for threaded attachment to the threads 625 on the ultrasonic horn portion 624. As can be further seen in FIG. 11, a proximal end 626 of the transducer housing 620 may have threads 627 formed thereon for threaded attachment to a threaded bushing 640. Threaded bushing 640 may have an axial passage 642 therethrough for receiving a rotatable tissue cutting or "shaver" blade 650 therethrough. In various embodiments, the shaver blade 650 may be fabricated from, for example, aluminum, titanium, aluminum alloys, steels, ceramics, etc. and be rotatably supported within the transducer housing 620 by a bearing 651 that is located at a node "N" in the housing 620. The proximal end 652 of the shaver blade 650 may be attached to a motor 660. The shaver blade 650 may for example, be attached to a drive shaft 662 of the motor 660 by threads (not shown) or other suitable coupling arrangement. The transducers 622 may receive power from the ultrasonic generator 12 in the control system 10 through conductors 628, 629. Motor 660 may communicate with the various components in the control system 10 through conductors 664, 665.

In various embodiments, the shaver blade 650 may have a distal end 654 that may be configured to cut tissue when the blade 650 is rotated about axis A-A. In one embodiment, for example, the distal end 654 has a series of teeth 656 formed thereon. See FIG. 12. Also in various embodiments, the shaver blade 650 may have an axial suction lumen 657 therethrough. At least one discharge hole 658 is provided through the shaver blade 650 to enable the suction lumen 657 to discharge cut tissue and fluids therethrough into a suction chamber 670 located within the housing 602. The suction chamber 670 may be sealingly attached to the bushing 640 or be otherwise supported within the housing 602 such that the shaver blade 650 extends therethrough. Because the bushing 640 is part of the acoustic system and attachment of the suction chamber 670 to the bushing 640 would make it part of the acoustic system as well, it is desirable for the connection between the suction chamber 670 and the bushing 640 to be located at a Node of vibration. In the embodiment depicted in FIG. 11, a shaft seal 672 may be provided on the shaver blade 650 to establish a substantially fluid-tight seal between the shaver blade 650 and the suction chamber 670. In various embodiments, the shaft seal 672 may be fabricated from, for example, silicone rubber, epdm rubber, Teflon®, Ultem®, etc. The suction chamber 670 may discharge through a flexible hose 674 that communicates with a collection receptacle 676 and a source of suction 678.

The instrument 600 may further have an acoustically isolated hollow sheath 680 that extends from the housing 602 to cover a substantial portion of the ultrasonic blade 630. That is, in various embodiments, the hollow sheath 680 may cover all of the ultrasonic blade 630 except for a distal end portion 634 that has a blade opening 635 therein. See FIG. 12. The hollow sheath 680 may be fabricated from flouroethylene-propelene (FEP), silicon or similar materials that can acoustically isolate or acoustically insulate the outside of the ultrasonic blade 630. At least one seal 636 may be employed between the outer sheath 680 and the ultrasonic blade 630. Similarly, the ultrasonic blade 630 may be isolated from the shaver blade 650 by at least one seal 651. In various embodiments, the seals 636, 651 may comprise one or more seals of the type described in co-pending U.S. patent application Ser. No. 12/703,866, entitled SEAL ARRANGEMENTS FOR ULTRASONICALLY POWERED SURGICAL INSTRUMENTS, now U.S. Patent Application Publication No. 2011/0196398, which has been herein incorporated by reference in its entirety. As can also be seen in FIGS. 11 and 12, the distal end portion 634 of the ultrasonic blade 630 may be substantially blunt or rounded.

When power is supplied to the motor 660, the drive shaft 662 rotates about axis A-A which also causes the shaver blade 650 to rotate about axis A-A. Activation of the source of suction 678 causes suction to be applied to the suction lumen 657 in the shaver blade 650 to draw tissue into the opening 635 in the hollow sheath 680 and into contact with the rotating shaver blade 650. The source of suction 678 may communicate with and be controlled by the control system 10 such that suction is only applied to the lumen 657 when the shaver blade 650 is being rotated by motor 660.

The surgical instrument 600 may have two primary modes of operation. One mode is the shaver mode, in which the shaver blade 650 rotates in concert with suction to cut tissue that enters the opening 636. The other mode is the ultrasonic coagulation mode. As an ultrasonic instrument, the ultrasonic blade 630 is driven in a linear ultrasonic vibration mode by the transducers 622. The user is able to coagulate bleeders and tissue as needed with the exposed distal end 634 of the ultrasonic blade 630. In use, the instrument 600 can be activated in shaver modes independently or in ultrasonic mode independently. Both modes can also be activated together and suction can be turned on and off at any time. When using the instrument 600 in one of the ultrasonic modes, the distal end 634 of the ultrasonic blade 630 can be used to coagulate tissue while the remainder of the device can safely come in contact with tissue outside of the targeted site because it is not ultrasonically active.

FIGS. 13-17 illustrate another surgical instrument 700 of the present invention. The surgical instrument 700 may include a housing 702 that may be manufactured in multiple pieces from, for example, plastics such as polycarbonate, polyetherimide (GE Ultem®) or metals such as aluminum, titanium or steel that are coupled together by fasteners such as screws, bolts, snap features or may be retained together by adhesive, welding, etc. As can be seen in FIGS. 13 and 15-17, the housing 702 may define a suction chamber 703 that communicates with a suction port 705. A flexible tube or other suitable conduit 707 may be coupled to the suction port 705 as well as to a collection receptacle 709 that may be located within the surgical suite. The collection receptacle 709 may be coupled to a source of suction 711 to apply suction to the suction chamber 703 through the flexible tube 707 and suction port 705. A motor 710 of the type and construction described above may also be supported within the housing 702. The motor 710 has a drive shaft 712 that extends into the suction chamber 703. The drive shaft 712 may be supported by a bearing 714 in a wall of the suction chamber 703. A seal 716 may also be employed to achieve a substantially fluid-tight seal between the drive shaft 712 and the wall of the suction chamber 703. The motor 710 may communicate with the various components of the control system 10 through conductors 717, 718 in the manner discussed above.

Figure 13:
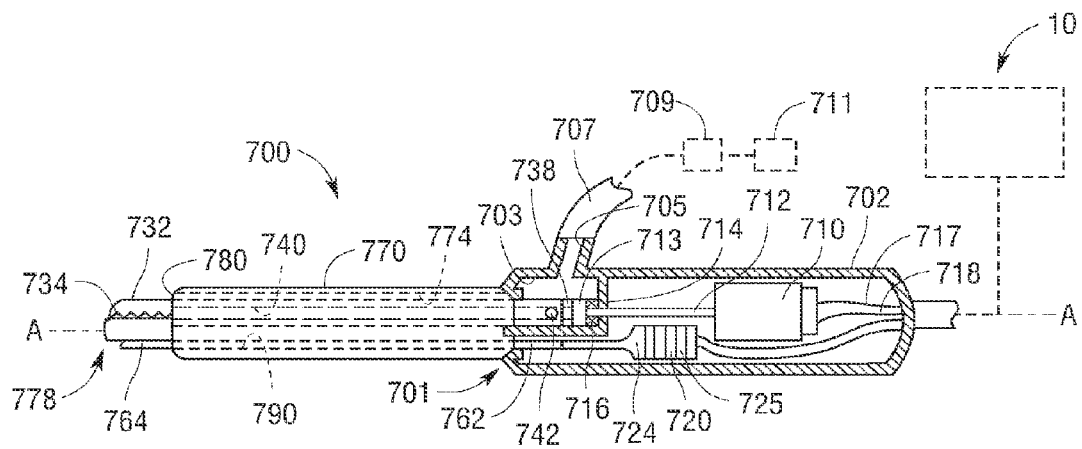
FIG. 13 is a side elevational view of another non-limiting surgical instrument embodiment of the present invention with portions thereof shown in cross-section.
Figure 14:
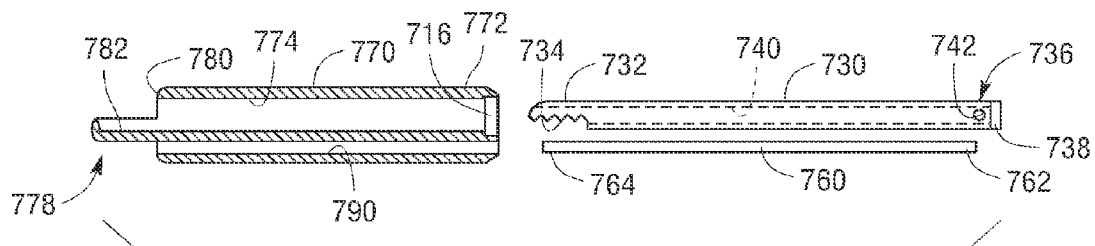
FIG. 14 is an exploded assembly view of an outer sheath assembly and a shaver blade and an ultrasonic blade of various non-limiting embodiments of the present invention with the outer sheath shown in cross-section.
Figure 15:
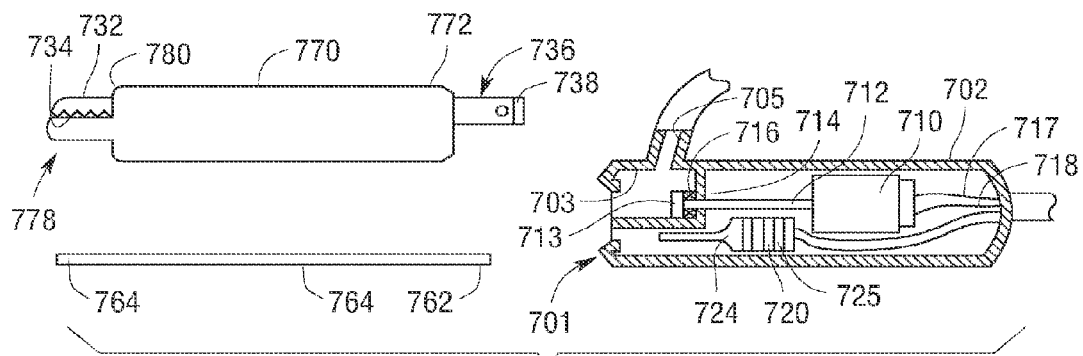
FIG. 15 is an exploded assembly view of the surgical instrument of FIG. 13.

An ultrasonic transducer assembly 720 that has an ultrasonic horn portion 722 attached thereto or integrally formed therewith may also be supported within the housing 702. The ultrasonic transducer assembly 720 may comprise at least one and preferably a stack of, for example, four to eight lead zirconate titanate (PZT-8) ceramic piezoelectric elements 725 with a motion null point located at some point along the stack. In various embodiments, for example, a series of internal threads (not shown) may be formed on the distal end portion of the horn portion 722 for attachment to an ultrasonic blade 760. Ultrasonic blade 760 may have a threaded proximal end 762 for threaded attachment to the horn portion 722 as will be discussed in further detail below. The surgical instrument 700 may further include a hollow tissue cutting or "shaver" blade 730 that may be fabricated from, for example, aluminum, titanium, aluminum alloys, titanium alloys, steels, ceramics, etc. A distal end 732 of the shaver blade 730 may have serrations 734 formed thereon or, in other embodiments, the serrations may be omitted. In some embodiments, a proximal end 736 of the shaver blade 730 may be fabricated for removable attachment to the drive shaft 712 of the motor 710. In one embodiment, for example, a "quarter-twist" or bayonet-type coupling 738 may be employed to couple the proximal end 736 of the shaver blade 730 to a corresponding coupling portion 713 that is attached to the drive shaft 712. Such bayonet coupling arrangements are known and may facilitate coupling of the shaver blade 730 to the drive shaft 712 by engaging the coupling portions 738, 713 and rotating the blade 730 while the drive shaft 712 remains stationary. Other forms of coupling arrangements could also be successfully employed without departing from the spirit and scope of the present invention. The shaver blade 730 may further have a suction lumen 740 that extends therethrough. At least one suction hole 742 may provided in the proximal end 736 of the shaver blade 730 to enable the suction lumen 740 extending therethrough to discharge into the suction chamber 703 when the proximal end 736 is coupled to the drive shaft 712 as illustrated in FIG. 13.

In various embodiments, the surgical instrument 700 may further include an outer sheath assembly 770 that may be fixedly attached to the housing 702. In one embodiment, for example, the proximal end 772 of the outer sheath assembly 770 may include a quarter-turn or bayonet-type coupling arrangement that is configured for attachment to the distal end 701 of the housing 702. However, other known coupling arrangements may be employed for removably coupling the outer sheath assembly 770 to the housing 702 without departing from the spirit and scope of the present invention. As can be most particularly seen in FIG. 14, the outer sheath assembly 770 may have a shaver blade lumen 774 that extends therethrough and which is sized to rotatably receive the shaver blade 730 therein. Various embodiments may also employ a bearing 776 in the proximal end 772 of the outer sheath assembly 770 for rotatably supporting the shaver blade 730 therein. Additional bearing and/or seal arrangements may be employed to rotatably support the shaver blade 730 within the outer sheath assembly 770. The distal end 778 of the outer sheath assembly 770 may also have an opening 780 therein to expose the distal end 732 of the shaver blade 730. The distal end 778 of the outer sheath assembly 770 may also form a cutting board surface 782 upon which the distal end 732 of the shaver blade 730 may oscillate. The outer sheath assembly 770 may further have an ultrasonic blade lumen 790 for receiving the ultrasonic blade 760 therein. The ultrasonic blade lumen 790 may be substantially parallel to the shaver blade lumen 774. One or more seal members (not shown) of the type and construction described in the aforementioned pending patent applications that have been incorporated herein by reference or others may be employed to support the ultrasonic blade 760 within the ultrasonic blade lumen 790 while achieving a substantially fluid tight seal between the blade 760 and the lumen 790.

Figure 16:
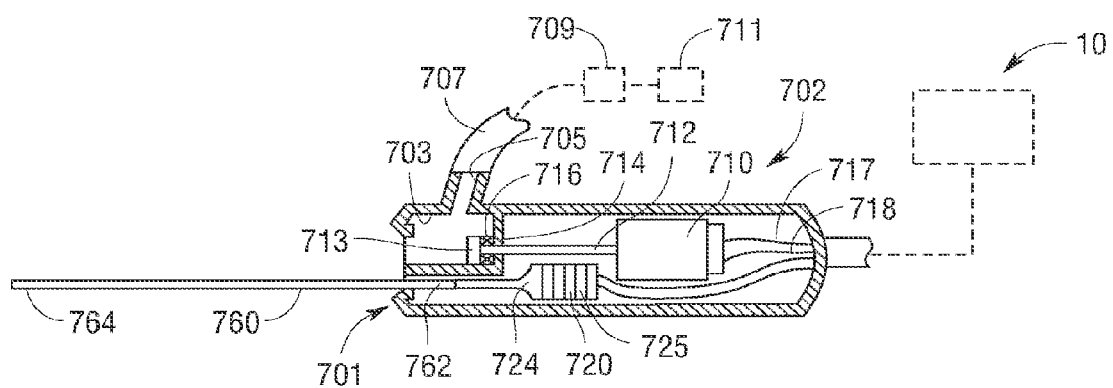
FIG. 16 is a cross-sectional view of a portion of the surgical instrument of FIGS. 13 and 15 with the ultrasonic blade attached thereto.
Figure 17:
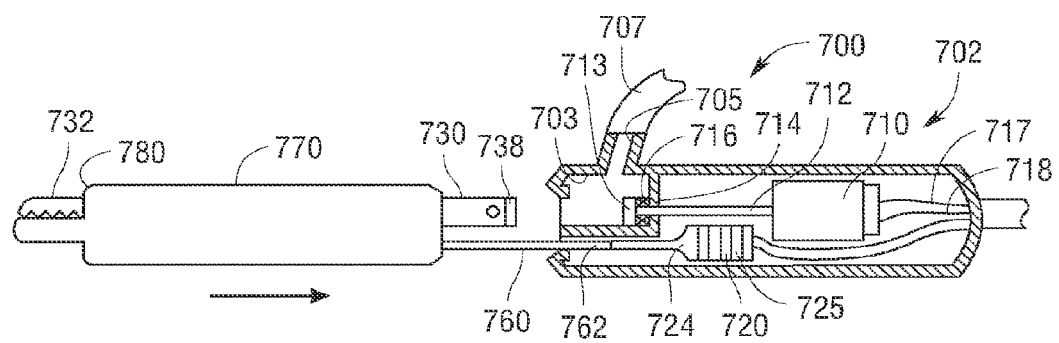
FIG. 17 is another view of the surgical instrument of FIG. 16 with the outer sheath assembly being slid over the ultrasonic blade.

Assembly of the instrument 700 will now be explained with reference to FIGS. 16 and 17. As can be seen in FIG. 16, for example, the proximal end 762 of the ultrasonic blade 760 is attached to the ultrasonic horn 722. In one embodiment, the proximal end 762 of the ultrasonic blade 760 is threaded onto the ultrasonic horn 722. In still other embodiments, however, the ultrasonic blade 760 may be integrally formed with the ultrasonic horn 722. After the ultrasonic blade 760 is coupled to the ultrasonic horn 722, the outer sheath assembly 770 with the shaver blade 730 supported therein is oriented such that the distal end 764 of the ultrasonic blade 760 is introduced into the lumen 790. The outer sheath assembly 770 is then slid over the ultrasonic blade 760 to bring the proximal end 772 of the outer sheath assembly 770 into engagement with the distal end 701 of the housing 702. The outer sheath assembly 770 may then be manipulated in a known manner to couple the bayonet-type coupling arrangement together. In other embodiments, the outer sheath assembly 770 may be permanently fixed to the housing 702 with adhesive, welding, etc. In still other arrangements, the outer sheath assembly 770 may be attached to the housing 702 with removable fasteners such as screws, bolts, etc.

In use, the control system 10 components may be employed to control motor 710 such that the drive shaft 712 is caused to oscillate back and forth about axis A-A which also causes the shaver blade 730 to rotate about axis A-A. Activation of the source of suction 711 may cause suction to be applied to the suction lumen 740 in the shaver blade 730 to draw tissue into contact with the oscillating distal end 732 of the shaver blade 730. Pieces of severed tissue may be drawn in through the suction lumen 740 and ultimately be collected in the collection receptacle 709. If hemostasis is desired, the surgeon can activate the ultrasonic transducer assembly 720 to ultrasonically power the ultrasonic blade 760. The distal end 764 of the ultrasonic blade 760 that protrudes out of the outer sheath assembly 770 (FIG. 13) may then be pressed against the bleeding tissue to utilize the ultrasonic energy to stop the bleeding.

Figure 18:
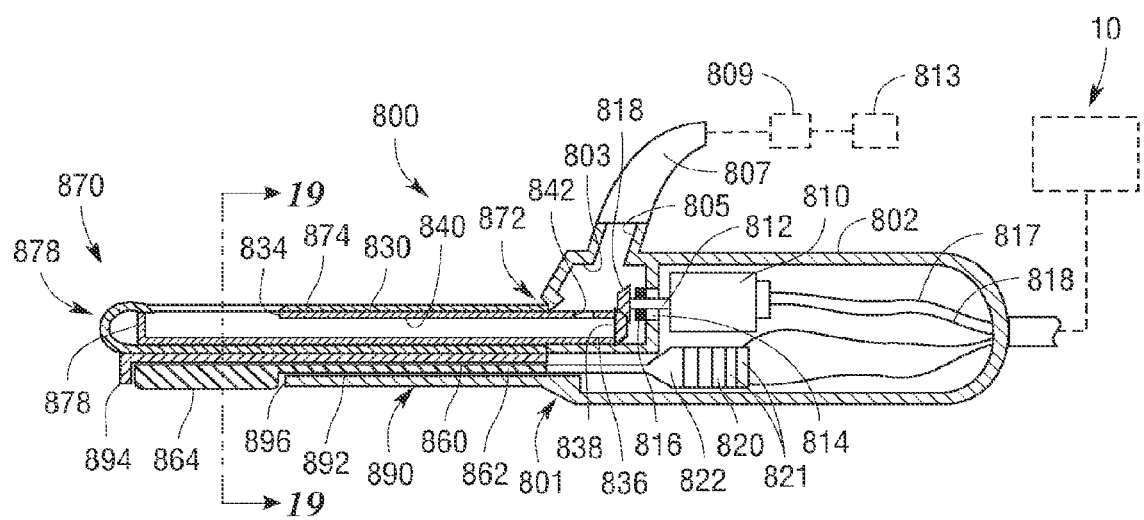
FIG. 18 is a cross-sectional view of another non-limiting surgical instrument embodiment of the present invention.
Figure 19:
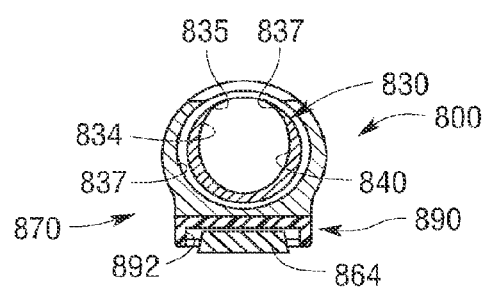
FIG. 19 is a cross-sectional end view of the surgical instrument of FIG. 18 taken along line 19-19 in FIG. 18.

FIGS. 18 and 19 illustrate another surgical instrument 800 of the present invention. The surgical instrument 800 may include a housing 802 that may be manufactured in multiple pieces from, for example, plastics such as polycarbonate, polyetherimide (GE Ultem®) or metals such as aluminum, titanium or steel that are coupled together by fasteners such as screws, bolts, snap features or may be retained together by adhesive, welding, etc. As can be seen in FIG. 18, the housing 802 may define a suction chamber 803 that communicates with a suction port 805. A flexible tube or other suitable conduit 807 may be coupled to the suction port 805 as well as to a collection receptacle 809. The collection receptacle 809 may be coupled to a source of suction 811 for applying suction to the suction chamber 803 through the flexible tube 807 and suction port 805. A motor 810 of the type and construction described above may also be supported within the housing 802. The motor 810 has a motor drive shaft 812 that extends into the suction chamber 803. The motor drive shaft 812 may be supported by a bearing 814 in a wall of the suction chamber 803. A seal 816 may also be employed to achieve a substantially fluid-tight seal between the drive shaft 812 and the wall of the suction chamber 803. The motor 810 may communicate with the various components of the control system 10 through conductors 817, 818 in the various manners described above.

Also supported in the housing 802 is an ultrasonic transducer assembly 820 that has an ultrasonic horn portion 822 attached thereto or integrally formed therewith. The ultrasonic transducer assembly 820 may comprise at least one and preferably a stack of, for example, four to eight lead zirconate titanate (PZT-8) ceramic piezoelectric elements 821 with a motion null point located at some point along the stack. In various embodiments, the ultrasonic blade 860 may be attached to the distal end of the horn portion 822 by, for example, a screw fitting. The surgical instrument 800 may further include a hollow shaver blade 830 that may be fabricated from, for example, aluminum, titanium, aluminum alloys, titanium alloys, steels, ceramics, etc. A distal end 832 of the shaver blade 830 may have an opening 834 therein that forms two sharp tissue cutting edges 835, 837 as shown in FIG. 19. A proximal end 836 of the shaver blade 830 may have a driven gear 838 that is retained in meshing engagement with a drive gear 818 attached to the drive shaft 812 of the motor 810. The shaver blade 830 may further have a suction lumen 840 that extends therethrough. At least one suction hole 882 may be provided in the proximal end 836 of the shaver blade 830 to discharge into the suction chamber 803 when the proximal end 836 is coupled to the drive shaft 812 as illustrated in FIG. 18.

In various embodiments, the surgical instrument 800 may further include a shaver blade sheath 870 that may be fixedly attached to the housing 802. In one embodiment the proximal end 872 of the shaver blade sheath 870 may be fabricated from, for example, a metal material such as aluminum, titanium, steels, titanium alloys or aluminum alloys and include a quarter-turn or bayonet-type coupling arrangement that is configured for attachment to the distal end 801 of the housing 802. However, other known coupling arrangements may be employed for removably coupling the shaver blade sheath 870 to the housing 802 without departing from the spirit and scope of the present invention. As can be most particularly seen in FIG. 18, the shaver blade sheath 870 may have a shaver blade lumen 874 extending therethrough that is sized to rotatably receive the shaver blade 830 therein. Various embodiments may also employ a bearing (not shown) in the proximal end of the shaver blade sheath 870 for rotatably supporting the shaver blade 830 within the shaver blade sheath 870. Additional bearing and/or seal arrangements may be employed to rotatably support the shaver blade 830 within the shaver blade sheath 870. The distal end 878 of the shaver blade sheath 870 may for a substantially blunt closed end that has an opening 880 therein to expose the distal end 832 of the shaver blade 830.

Also in this embodiment, an ultrasonic blade sheath 890 may be attached to the housing 802. In various embodiments, for example, the ultrasonic blade sheath 890 may be fabricated from a polymer material such as polyetherimide, liquid crystal polymers, polycarbonate, nylon or ceramic material and be attached to the housing 802 by screw threads, bonding, press fitting, crimping, etc. The ultrasonic blade sheath 890 may further have an ultrasonic blade lumen 892 extending therethrough for receiving the ultrasonic blade 860 therein. One or more seal members (not shown) of the type and construction described in the aforementioned pending patent applications that have been incorporated by reference or others may be employed to support the ultrasonic blade 860 within the lumen 892 while achieving a substantially fluid-tight seal between the blade 860 and the lumen 892. The ultrasonic blade sheath 890 may further have an opening 896 in a distal end 894 to expose a distal end 864 of the ultrasonic blade 860.

In use, the control system 10 components may be used to control motor 810 such that the drive shaft 812 is rotated about axis A-A which also causes the shaver blade 830 to rotate about axis A-A. Activation of the source of suction 811 will cause suction to be applied to the suction lumen 840 in the shaver blade 830 to draw tissue in through the opening 880 in the distal end 878 of the shaver blade sheath 870 and into the opening 834 in the shaver blade 830. Pieces of severed tissue may be drawn in through the suction lumen 840 and ultimately be collected in the collection receptacle 809. If hemostasis is desired, the surgeon can activate the ultrasonic transducer assembly 820 to ultrasonically power the ultrasonic blade 860. The distal end 864 that protrudes out of the ultrasonic sheath assembly 890 (FIG. 19) may then be pressed against the bleeding tissue to utilize the ultrasonic energy to stop the bleeding.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

All of the above U.S. patents and U.S. patent applications, and published U.S. patent applications referred to in this specification are incorporated herein by reference in their entirety, but only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ultrasonic surgical instrument, comprising:
   a housing;
   a cutting blade;
   at least one ultrasonic transducer contained within said housing and supported for axial displacement within said housing; and
   an ultrasonic blade protruding from said at least one ultrasonic transducer, wherein axial displacement of said at least one ultrasonic transducer is configured to axially displace said ultrasonic blade relative to said cutting blade.

2. The ultrasonic surgical instrument of claim 1, wherein said cutting blade is supported for selective rotational displacement relative to said housing, and wherein said ultrasonic surgical instrument further comprises an outer sheath coupled to said housing and supporting said cutting blade therein, said outer sheath having a closed distal end with a distal tissue opening therein to expose a distal tissue cutting portion of said cutting blade and wherein a distal end of said ultrasonic blade protrudes through an opening in said closed distal end of said outer sheath.

3. The ultrasonic surgical instrument of claim 2, wherein at least a portion of said distal end of said ultrasonic blade that protrudes through said opening in said outer sheath is rounded.

4. The ultrasonic surgical instrument of claim 1, comprising a motor, wherein said ultrasonic blade extends through a hollow passage in said motor.

5. The ultrasonic surgical instrument of claim 4, wherein said at least one ultrasonic transducer is housed within a transducer housing coupled to said motor.

6. The ultrasonic surgical instrument of claim 5, wherein said transducer housing is attached to said motor by a magnetic coupling arrangement.

7. The ultrasonic surgical instrument of claim 1, comprising an actuator member coupled to said housing and interacting with said at least one ultrasonic transducer to facilitate the selective gross axial movement of said at least one ultrasonic transducer relative to said housing.

8. The ultrasonic surgical instrument of claim 1, wherein said cutting blade has a plurality of cutting edges formed thereon.

9. An ultrasonic surgical instrument, comprising:
   a housing;
   at least one ultrasonic transducer contained within said housing and supported for axial displacement within said housing;
   an ultrasonic blade coupled to said at least one ultrasonic transducer, wherein axial displacement of said at least one ultrasonic transducer is configured to axially displace said ultrasonic blade; and
   a cutting blade.

10. The ultrasonic surgical instrument of claim 9, wherein said cutting blade has a suction lumen therein that communicates with a source of suction.

11. The ultrasonic surgical instrument of claim 10, comprising a suction chamber within said housing, said suction chamber communicating with said source of suction and said suction lumen in said cutting blade.

12. The ultrasonic surgical instrument of claim 10, comprising an outer sheath coupled to said housing such that said ultrasonic blade extends therethrough and at least a portion of a distal end of said ultrasonic blade extends distally out of said outer sheath.

13. The ultrasonic surgical instrument of claim 12, wherein said outer sheath is connected to said ultrasonic blade by an acoustically isolating material.

14. The ultrasonic surgical instrument of claim 12, wherein said outer sheath is in direct contact with said ultrasonic blade.

15. The ultrasonic surgical instrument of claim 9, comprising a motor coupled to said cutting blade for axially moving said cutting blade within said ultrasonic blade.

16. An ultrasonic surgical instrument, comprising:
a housing;
a cutting blade;
at least one ultrasonic transducer contained within said housing; and
an ultrasonic blade protruding from said at least one ultrasonic transducer, said ultrasonic blade being substantially parallel to said cutting blade.

17. The ultrasonic surgical instrument of claim 16, wherein said cutting blade has a suction lumen extending therethrough that communicates with a source of suction.

18. The ultrasonic surgical instrument of claim 16, wherein said cutting blade is supported within a cutting blade lumen in a cutting blade outer sheath attached to said housing and wherein said ultrasonic blade extends through an ultrasonic blade lumen in an ultrasonic outer sheath attached to said housing.

19. The ultrasonic surgical instrument of claim 18, wherein said cutting blade outer sheath is made from a first material and wherein said ultrasonic outer sheath is made from a second material that differs from said first material.

* * * * *